United States Patent
Boehringer et al.

(10) Patent No.: US 7,122,555 B2
(45) Date of Patent: Oct. 17, 2006

(54) PYRIDO [2,1-A] ISOQUINOLINE DERIVATIVES

(75) Inventors: Markus Boehringer, Moehlin (CH); Bernd Kuhn, Riehen (CH); Patrizio Mattei, Riehen (CH); Robert Narquizian, St. Louis (FR)

(73) Assignee: Hoffmann-la Roche Inc., Nutley, NJ (US)

( * ) Notice: Subject to any disclaimer, the term of this patent is extended or adjusted under 35 U.S.C. 154(b) by 94 days.

(21) Appl. No.: 10/870,580

(22) Filed: Jun. 17, 2004

(65) Prior Publication Data

US 2004/0259903 A1 Dec. 23, 2004

(30) Foreign Application Priority Data

Jun. 20, 2003 (EP) ................. 03013404

(51) Int. Cl.
- *A01N 43/42* (2006.01)
- *A61K 31/44* (2006.01)
- *C07D 455/06* (2006.01)
- *C07D 455/00* (2006.01)
- *C07D 453/00* (2006.01)

(52) U.S. Cl. ............. 514/294; 546/95; 546/94
(58) Field of Classification Search ........ 546/95, 546/94; 514/294
See application file for complete search history.

(56) References Cited

U.S. PATENT DOCUMENTS

| | | | |
|---|---|---|---|
| 5,455,351 A | 10/1995 | Kempf et al. | |
| 6,011,155 A | 1/2000 | Villhauer | |
| 6,110,949 A | 8/2000 | Villhauer | |
| 6,124,305 A | 9/2000 | Villhauer | |
| 6,303,661 B1 | 10/2001 | Demuth et al. | |
| 6,319,893 B1 | 11/2001 | Demuth et al. | |
| 6,727,261 B1 * | 4/2004 | Gobbi et al. ............. | 514/294 |
| 2002/0071838 A1 | 6/2002 | Demuth et al. | |

FOREIGN PATENT DOCUMENTS

| | | |
|---|---|---|
| DE | 19616486 A1 | 10/1997 |
| DE | 19616486 C2 | 10/1997 |
| DE | 19834591 | 2/2000 |
| EP | 1 308 439 A1 | 5/2003 |
| WO | WO 95/01976 | 1/1995 |
| WO | WO 96/10018 | 4/1996 |
| WO | WO 98/19998 | 5/1998 |
| WO | WO 99/38501 A2 | 8/1999 |
| WO | WO 99/38501 A3 | 8/1999 |
| WO | WO 00/08002 | 2/2000 |
| WO | WO 0034241 | 6/2000 |
| WO | WO 01/19805 | 3/2001 |
| WO | WO 0134594 | 5/2001 |
| WO | WO 01/40180 | 6/2001 |
| WO | WO 01/55105 | 8/2001 |
| WO | WO 0162266 | 8/2001 |
| WO | WO 0230890 | 4/2002 |

OTHER PUBLICATIONS

Agarwal, A., et. al., Synth. Commun. (1993) 23, 1101-1110.
Ali, et. al., Pak. J. Sci. Ind. Res., 36, pp. 502-510 (1993).
Carrera, G.M., et. al., Synlett (1994) 1, 93-94.
Collins, J.L., et. al. J. Med Chem. (1998) 41, 5037-5054.
Freedman, J., et. al., J. Heterocycl. Chem. (1990) 27, 343-346.
Francis, et. al., Tetrahedron Ltrs., 28, pp. 5133-5136 (1987).
Golfier, et. al., J. Heterocycl. Chem., 10, pp. 989-991 (1973).
Goto, et. al., Chem. Pharm. Bull, 19, pp. 2050-2057 (1971).
Helv. Chim. Acta (1958) 41, 119.
Horne, et. al., Heterocycles, 39, pp. 139-153 (1994).
Lipp, et. al., Eur. J. Med. Chem., 30 pp. 219-225 (1995).
Novartis AG, Expert Opinion on Therapeutic Patents, Ashley Publications, GB, vol. 10, No. 12, pp. 1937-1942 (2000).
Qizhuang, Y., et.al., J. Med. Chem. (1989) 32, 478-486.
P. Kocienski, Protecting Groups, Thieme Verlag Stuttgart, NY (1994) pp. 192-201.
Schunack, et. al., Z. Naturforschung, 42b, pp. 238-242 (1987).
Singh, et. al., Ind. J. Chem., 22B, pp. 1177-1178 (1983).
TETRAHEDRON (1974), 30, 2157.
TETRAHEDRON Lett. (1984) 25, 3515.
Weintraub, P. M., J. Med. Chem, 15, pp. 419-420 (1972).
Chem. Ber 95, 2132 (1962).
J. Org. Chem (1998) 63, 6715.

* cited by examiner

*Primary Examiner*—D. Margaret Seaman
*Assistant Examiner*—Niloofar Rahmani
(74) *Attorney, Agent, or Firm*—George W. Johnston; Dennis P. Tramaloni; Samuel H. Megerditchian

(57) ABSTRACT

The present invention provides compounds of formula (I)

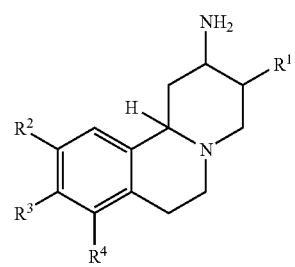

wherein $R^1$, $R^2$, $R^3$ and $R^4$ are as indicated in the description, or a pharmaceutically acceptable salt thereof. The compounds are useful for the treatment of diseases which are associated with DPP-IV, such as diabetes, particularly non-insulin dependent diabetes mellitus, and impaired glucose tolerance.

24 Claims, No Drawings

PYRIDO [2,1-A] ISOQUINOLINE DERIVATIVES

BACKGROUND OF THE INVENTION

The enzyme dipeptidyl peptidase IV (EC.3.4.14.5, abbreviated in the following as DPP-IV) is involved in the regulation of the activities of several hormones. In particular DPP-IV is degrading efficiently and rapidly glucagon like peptide 1 (GLP-1), which is one of the most potent stimulator of insulin production and secretion. Inhibiting DPP-IV would potentiate the effect of endogenous GLP-1, and lead to higher plasma insulin concentrations. In patients suffering from impaired glucose tolerance and type 2 diabetes mellitus, higher plasma insulin concentration would moderate the dangerous hyperglycaemia and accordingly reduce the risk of tissue damage. Consequently, DPP-IV inhibitors have been suggested as drug candidates for the treatment of impaired glucose tolerance and type 2 diabetes mellitus (e.g. Villhauer, WO98/19998). Other related state of the art can be found in WO 99/38501, DE 19616486, DE 19834591, WO 01/40180, WO 01/55105, U.S. Pat. No. 6,110,949, WO 00/34241 and U.S. Pat. No. 6,011,155.

SUMMARY OF THE INVENTION

The present invention provides compounds of the formula (I)

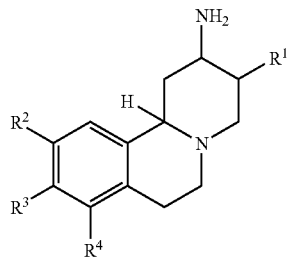

wherein $R^1$ is —C(O)—N($R^5$)$R^6$ or —N($R^5$)$R^6$;

$R^2$, $R^3$ and $R^4$ are each independently hydrogen, halogen, hydroxy, lower alkyl, lower alkoxy or lower alkenyl, wherein lower alkyl, lower alkoxy and lower alkenyl may optionally be substituted by lower alkoxycarbonyl, aryl or heterocyclyl;

$R^5$ is hydrogen, lower alkyl, halogenated lower alkyl or cycloalkyl;

$R^6$ is lower alkylsulfonyl, halogenated lower alkylsulfonyl, cycloalkylsulfonyl, lower alkylcarbonyl, halogenated lower alkylcarbonyl, cycloalkylcarbonyl; or $R^5$ and $R^6$ together with the nitrogen atom to which they are attached form a 4-, 5-, 6- or 7-membered saturated or unsaturated non-aromatic heterocyclic ring optionally containing a further heteroatom selected from nitrogen, oxygen and sulfur, said heterocyclic ring being optionally mono-, di-, or tri-substituted, independently, with lower alkyl, halogenated lower alkyl, oxo, dioxo and/or cyano;

or a pharmaceutically acceptable salt thereof.

Compounds of the present invention are DPP-IV inhibitors that lower plasma glucose levels, and are useful in the treatment of non-insulin dependent diabetes mellitus.

DETAILED DESCRIPTION OF THE INVENTION

We have found novel DPP-IV inhibitors that very efficiently lower plasma glucose levels. Consequently, the compounds of the present invention are useful for the treatment and/or prophylaxis of diabetes, particularly non-insulin dependent diabetes mellitus, and/or impaired glucose tolerance, as well as other conditions wherein the amplification of action of a peptide normally inactivated by DPP-IV gives a therapeutic benefit. Surprisingly, the compounds of the present invention can also be used in the treatment and/or prophylaxis of obesity, inflammatory bowel disease, Colitis Ulcerosa, Morbus Crohn, and/or metabolic syndrome or β-cell protection. Furthermore, the compounds of the present invention can be used as diuretic agents and for the treatment and/or prophylaxis of hypertension.

Unexpectedly, the compounds of the present invention exhibit improved therapeutic and pharmacological properties compared to other DPP-IV inhibitors known in the art, such as e.g. in context with pharmacokinetics and bioavailability.

The present invention provides a compound of formula (I)

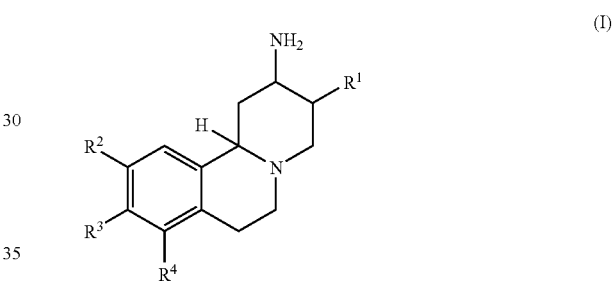

wherein $R^1$ is —C(O)—N($R^5$)$R^6$ or —N($R^5$)$R^6$;

$R^2$, $R^3$ and $R^4$ are each independently hydrogen, halogen, hydroxy, lower alkyl, lower alkoxy, lower alkenyl, substituted lower alkyl, substituted lower alkoxy, or substituted lower alkenyl, wherein substituted lower alkyl, substituted lower alkoxy and substituted lower alkenyl are lower alkyl, lower alkoxy and lower alkenyl, respectively, which are independently substituted by a group selected from the group consisting of lower alkoxycarbonyl, aryl and heterocyclyl;

$R^5$ is hydrogen, lower alkyl, halogenated lower alkyl or cycloalkyl;

$R^6$ is lower alkylsulfonyl, halogenated lower alkylsulfonyl, cycloalkylsulfonyl, lower alkylcarbonyl, halogenated lower alkylcarbonyl, or cycloalkylcarbonyl; or $R^5$ and $R^6$ together with the nitrogen atom to which they are attached form a 4-, 5-, 6- or 7-membered saturated or unsaturated non-aromatic heterocyclic ring optionally containing a further heteroatom selected from nitrogen, oxygen and sulfur, said heterocyclic ring being optionally mono-, di-, or tri-substituted, independently, with a group selected from the group consisting of lower alkyl, halogenated lower alkyl, oxo, dioxo and cyano;

or a pharmaceutically acceptable salt thereof.

Unless otherwise indicated, the following definitions are set forth to illustrate and define the meaning and scope of the various terms used to describe the invention herein. In this specification the term "lower" is used to mean a group consisting of one to six, preferably of one to four carbon atom(s).

The term "halogen" refers to fluorine, chlorine, bromine and iodine, with fluorine, bromine and chlorine being preferred. Most preferred halogen is fluorine.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl", alone or in combination with other groups, refers to a branched or straight-chain monovalent alkyl radical of one to six carbon atoms, preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like. Preferable lower alkyl residues are methyl and ethyl, with methyl being especially preferred.

The term "halogenated lower alkyl" refers to a lower alkyl group wherein at least one of the hydrogens of the lower alkyl group is replaced by a halogen atom, preferably fluoro or chloro, most preferably fluoro. Among the preferred halogenated lower alkyl groups are trifluoromethyl, difluoromethyl, fluoromethyl and chloromethyl, with fluoromethyl being especially preferred.

The term "alkoxy" refers to the group R'—O—, wherein R' is alkyl. The term "lower-alkoxy" refers to the group R'—O—, wherein R' is lower-alkyl. Examples of lower alkoxy groups are e.g. methoxy, ethoxy, propoxy, isopropoxy, butoxy, isobutoxy and hexyloxy, with methoxy being especially preferred.

The term "lower alkoxycarbonyl" refers to the group R'—O—C(O)—, wherein R' is lower alkyl.

The term "aryl" refers to an aromatic monovalent mono- or polycarbocyclic radical, such as phenyl or naphthyl, preferably phenyl, which may optionally be mono-, di- or tri-substituted, independently, by lower alkyl, lower alkoxy, halo, cyano, azido, amino, di-lower alkyl amino or hydroxy.

The term "cycloalkyl" refers to a monovalent carbocyclic radical of three to six, preferably three to five carbon atoms. This term is further exemplified by radicals such as cyclopropyl, cyclobutyl, cyclopentyl and cyclohexyl, with cyclopropyl and cyclobutyl being preferred. Such cycloalkyl residues may optionally be mono-, di- or tri-substituted, independently, by lower alkyl or by halogen.

The term "heterocyclyl" refers to a 5- or 6-membered aromatic or saturated N-heterocyclic residue, which may optionally contain a further nitrogen or oxygen atom, such as imidazolyl, pyrazolyl, thiazolyl, pyridyl, pyrimidyl, morpholino, piperazino, piperidino or pyrrolidino, preferably pyridyl, thiazolyl or morpholino. Such heterocyclic rings may optionally be mono-, di- or tri-substituted, independently, by lower alkyl, lower alkoxy, halo, cyano, azido, amino, di-lower alkyl amino or hydroxy. Preferable substituent is lower alkyl, with methyl being preferred.

The term "a 4-, 5-, 6- or 7-membered saturated or unsaturated non-aromatic heterocyclic ring optionally containing a further heteroatom selected from nitrogen, oxygen and sulfur" refers to a non-aromatic heterocyclic ring, said heterocyclic ring being optionally mono-, di-, or tri-substituted, independently, with lower alkyl, halogenated lower alkyl, oxo, dioxo and/or cyano. Such saturated heterocyclic rings are for example pyrrolidinyl, piperidinyl, azepanyl, [1,2]thiazinanyl, [1,3]oxazinanyl, oxazolidinyl, thiazolidinyl or azetidinyl. Examples of such unsaturated heterocyclic rings are 5,6-dihydro-1H-pyridin-2-one, pyrrolinyl, tetrahydropyridine or dihydropyridine.

The term "pharmaceutically acceptable salts" embraces salts of the compounds of formula (I) with inorganic or organic acids such as hydrochloric acid, hydrobromic acid, nitric acid, sulphuric acid, phosphoric acid, citric acid, formic acid, maleic acid, acetic acid, fumaric acid, succinic acid, tartaric acid, methanesulphonic acid, salicylic acid, p-toluenesulphonic acid and the like, which are non toxic to living organisms. Preferred salts with acids are formates, maleates, citrates, hydrochlorides, hydrobromides and methanesulfonic acid salts, with hydrochlorides being especially preferred.

In one embodiment of the present invention, $R^1$ is —C(O)—N($R^5$)$R^6$. In another embodiment, $R^1$ is —N($R^5$)$R^6$.

In another embodiment, $R^2$, $R^3$ and $R^4$ are each independently hydrogen, hydroxy, lower alkoxy, or lower alkoxy substituted by aryl, by heterocyclyl or by lower alkoxycarbonyl. Preferable aryl residues in $R^2$, $R^3$ and $R^4$ are phenyl or phenyl substituted by di-lower alkylamino or by cyano. Preferable heterocyclyl residues in $R^2$, $R^3$ and $R^4$ are morpholino, pyridyl, thiazolyl or thiazolyl substituted by lower alkyl. Preferable lower alkoxycarbonyl residues in $R^2$, $R^3$ and $R^4$ are methoxycarbonly and ethoxycarbonly.

In another embodiment, $R^2$, $R^3$ and $R^4$ are each independently hydrogen, hydroxy or lower alkoxy.

In one preferable embodiment, residue $R^2$ is lower alkoxy, preferably methoxy, hydrogen or hydroxy. Most preferable residue $R^2$ is methoxy.

In another preferable embodiment, residue $R^3$ is lower alkoxy, with methoxy, ethoxy, propoxy, n-butoxy and isobutoxy being preferred, or hydrogen or hydroxy. Most preferable residue $R^3$ is methoxy or hydroxy, with methoxy being especially preferred.

In another preferable embodiment, residue $R^4$ is lower alkoxy, preferably methoxy, hydrogen or hydroxy. Most preferable residue $R^4$ is hydrogen.

In one embodiment, $R^5$ is hydrogen, lower alkyl, halogenated lower alkyl or cycloalkyl. Preferable lower alkyl residues in $R^5$ are methyl, ethyl, n-propyl, isopropyl, n-butyl, sec-butyl and tert-butyl, with methyl and ethyl being especially preferred. Preferable halogenated lower alkyl residues $R^5$ are fluoromethyl, 2-fluoroethyl and 3-fluoropropyl, with fluoromethyl being especially preferred. Preferred cycloalkyl residues $R^5$ are unsubstituted cyclopropyl and unsubstituted cyclobutyl. Preferably, $R^5$ is hydrogen, lower alkyl such as methyl or halogenated lower alkyl such as fluoromethyl.

In one embodiment, $R^6$ is lower alkylsulfonyl, halogenated lower alkylsulfonyl, cycloalkylsulfonyl, lower alkylcarbonyl, halogenated lower alkylcarbonyl, cycloalkylcarbonyl. Preferable lower alkylsulfonyl residues $R^6$ are methylsulfonyl, ethylsulfonyl and propylsulfonyl, with methylsulfonyl and ethylsulfonyl being especially preferred. Preferable lower alkylcarbonyl residues $R^6$ are methylcarbonyl, ethylcarbonyl and propylcarbonyl, with methylcarbonyl and ethylcarbonyl being especially preferred. Preferable halogenated lower alkylsulfonyl residues $R^6$ are ethylsulfonyl and propylsulfonyl. Preferable halogenated lower alkylcarbonyl residues $R^6$ are pentafluoroethylsulfonyl and 2,2,2-trifluoroethylsulfonyl. Preferable cycloalkylsulfonyl residues $R^6$ are cydopropylsulfonyl and cyclobutylsulfonyl. Preferable cycloalkylcarbonyl residues $R^6$ are cyclopropylcarbonyl and cyclobutylcarbonyl.

In a preferable embodiment, $R^6$ is lower alkylsulfonyl, preferably ethylsulfonyl, or lower alkylcarbonyl, preferably ethylcarbonyl, or cycloalkylcarbonyl, preferably cyclopropylcarbonyl.

In another embodiment, $R^5$ and $R^6$ together with the nitrogen atom to which they are attached form a 4-, 5-, 6- or 7-membered saturated or unsaturated heterocyclic ring optionally containing a further heteroatom selected from nitrogen, oxygen and sulfur, preferably sulfur, said heterocyclic ring being optionally mono-, di-, or tri-substituted, preferably mono- or di-substituted, independently, with lower alkyl such as methyl or ethyl, halogenated lower alkyl such as fluoromethyl, oxo, dioxo and/or cyano.

In still another embodiment, $R^5$ and $R^6$ together with the nitrogen atom to which they are attached form a 4-, 5-, 6- or 7-membered saturated or unsaturated heterocyclic ring optionally containing a sulfur atom or an oxygen atom as a further heteroatom in the ring, said heterocyclic ring being optionally mono- or di-substituted, independently, with lower alkyl such as methyl or ethyl, halogenated lower alkyl such as fluoromethyl, oxo, dioxo and/or cyano.

In a preferred embodiment, $R^5$ and $R^6$ together with the nitrogen atom to which they are attached are pyrrolidine, pyrrolidin-2-one, 4-methyl-pyrrolidin-2-one, 4-ethyl-pyrrolidin-2-one, 3-methyl-pyrrolidin-2-one, 5-methyl-pyrrolidin-2-one, 4-fluoro-methyl-pyrrolidin-2-one, pyrrolidine-2-carbonitrile, piperidine, piperidin-2-one, 4-methyl-piperidin-2-one, 5-methyl-piperidin-2-one, 5,6-dihydro-1H-pyridin-2-one, thiazolidin-3-yl, 1,1-dioxo-1,2-thiazolidin-2-yl, 1,1-dioxo[1,2]thiazinan-2-yl, azetidine, azepan-2-one, oxazolidin-2-one, 5-methyl-oxazolidin-2-one, 5-fluoromethyl-oxazolidin-2-one, or oxazinan-2-one. Most preferably, $R^5$ and $R^6$ together with the nitrogen atom to which they are attached are thiazolidin-3-yl, piperidin-2-one, 4-methyl-pyrrolidin-2-one, 4-fluoromethyl-pyrrolidin-2-one, 5,6-dihydro-1H-pyridin-2-one, 5-methyl-piperidin-2-one, 5-methyl-oxazolidin-2-one and 1,1-dioxo[1,2]thiazinan-2-yl.

In still another embodiment, the present invention is directed to compounds of formula I, wherein $R^1$ is —C(O)—N($R^5$)$R^6$ or —N($R^5$)$R^6$; $R^2$ is lower alkoxy such as methoxy; $R^3$ is lower alkoxy such as methoxy; and $R^4$ is hydrogen; and $R^5$ and $R^6$ together with the nitrogen atom to which they are attached form a 4-, 5-, 6- or 7-membered saturated or unsaturated heterocyclic ring optionally containing a sulfur atom as a further heteroatom in the ring, said heterocyclic ring being optionally mono- or di-substituted, independently, with lower alkyl such as methyl or ethyl, halogenated lower alkyl such as fluoromethyl, oxo, dioxo and/or cyano.

Preferred compounds of general formula (I) are those selected from the group consisting of:

(RS,RS,RS)-(2-amino-9,10-dimethoxy-1,3,4,6,7,11b-hexahydro-2H-pyrido[2,1-a]isoquinolin-3-yl)-pyrrolidin-1-yl-methanone, (RS,RS,RS)-(2-amino-9,10-dimethoxy-1,3,4,6,7,11b-hexahydro-2H-pyrido[2,1-a]isoquinolin-3-yl)-thiazolidin-3-yl-methanone, (RS,RS,RS)-(2-amino-9,10-dimethoxy-1,3,4,6,7,11b-hexahydro-2H-pyrido [2,1-a]isoquinolin-3-yl)-azetidin-1-yl-methanone, (SS)-1-((RS,RS,RS)-2-amino-9,10-dimethoxy-1,3,4,6,7,11b-hexahydro-2H-pyrido [2,1-a]isoquinoline-3-carbonyl)-pyrrolidine-2-carbonitrile, 1-((RS,RS,RS)-2-amino-9,10-dimethoxy-1,3,4,6,7,11b-hexahydro-2H-pyrido[2,1-a]isoquinolin-3-yl)-piperidin-2-one, (−)-(S,S,S)-1-(2-amino-9,10-dimethoxy-1,3,4,6,7,11b-hexahydro-2H-pyrido [2,1-a]isoquinolin-3-yl)-piperidin-2-one, (+)-(R,R,R)-1-(2-amino-9,10-dimethoxy-1,3,4,6,7,11b-hexahydro-2H-pyrido [2,1-a]isoquinolin-3-yl)-piperidin-2-one, 1-((RS,RS,RS)-2-amino-9,10-dimethoxy-1,3,4,6,7,11b-hexahydro-2H-pyrido[2,1-a]isoquinolin-3-yl)-4-methyl-piperidin-2-one, (RS,RS,RS)-1-(2-amino-9,10-dimethoxy-1,3,4,6,7,11b-hexahydro-2H-pyrido[2,1-a]isoquinolin-3-yl)-pyrrolidin-2-one, 1-((RS,RS,RS)-2-amino-9,10-dimethoxy-1,3,4,6,7,11b-hexahydro-2H-pyrido[2,1-a]isoquinolin-3-yl)-4-methyl-pyrrolidin-2-one, 1-((RS,RS,RS)-2-amino-9,10-dimethoxy-1,3,4,6,7,11b-hexahydro-2H-pyrido [2,1-a]isoquinolin-3-yl)-4-ethyl-pyrrolidin-2-one, (RS,RS,RS)-1-(2-amino-9,10-dimethoxy-1,3,4,6,7,11b-hexahydro-2H-pyrido [2,1-a]isoquinolin-3-yl)-5,6-dihydro-1H-pyridin-2-one, 1-((RS,RS,RS)-2-amino-9,10-dimethoxy-1,3,4,6,7,11b-hexahydro-2H-pyrido[2,1-a]isoquinolin-3-yl)-azepan-2-one, (RS,RS,RS)-3-(1,1-dioxo-1,2-thiazolidin-2-yl)-9,10-dimethoxy-1,3,4,6,7,11b-hexahydro-2H-pyrido[2,1-a]isoquinolin-2-ylamine, (RS,RS,RS)-3-(1,1-dioxo [1,2]thiazinan-2-yl)-9,10-dimethoxy-1,3,4,6,7,11b-hexahydro-2H-pyrido [2,1-a]isoquinolin-2-ylamine, (S,S,S)-3-(1,1-dioxo-[1,2]thiazinan-2-yl)-9,10-dimethoxy-1,3,4,6,7,11b-hexahydro-2H-pyrido [2,1-a]isoquinolin-2-ylamine, (SR)-1-((RS,RS,RS)-2-amino-9,10-dimethoxy-1,3,4,6,7,11b-hexahydro-2H-pyrido[2,1-a]isoquinolin-3-yl)-4-methyl-pyrrolidin-2-one, (RS,RS,RS,RS)-1-(2-amino-9,10-dimethoxy-1,3,4,6,7,11b-hexahydro-2H-pyrido[2,1-a]isoquinolin-3-yl)-4-methyl-pyrrolidin-2-one, (R)-1-((S,S,S)-2-amino-9,10-dimethoxy-1,3,4,6,7,11b-hexahydro-2H-pyrido[2,1-a]isoquinolin-3-yl)-4-methyl-pyrrolidin-2-one, (S)-1-((R,R,R)-2-amino-9,10-dimethoxy-1,3,4,6,7,11b-hexahydro-2H-pyrido [2,1-a]isoquinolin-3-yl)-4-methyl-pyrrolidin-2-one, (S,S,S,S)-1-(2-amino-9,10-dimethoxy-1,3,4,6,7,11b-hexahydro-2H-pyrido[2,1-a]isoquinolin-3-yl)-4-methyl-pyrrolidin-2-one, (R,R,R,R)-1-(2-amino-9,10-dimethoxy-1,3,4,6,7,11b-hexahydro-2H-pyrido [2,1-a]isoquinolin-3-yl)-4-methyl-pyrrolidin-2-one, 1-((RS,RS,RS)-2-amino-9,10-dimethoxy-1,3,4,6,7,11b-hexahydro-2H-pyrido[2,1-a]isoquinolin-3-yl)-4-fluoromethyl-pyrrolidin-2-one, 1-((RS,RS,RS)-2-amino-9,10-dimethoxy-1,3,4,6,7,11b-hexahydro-2H-pyrido[2,1-a]isoquinolin-3-yl)-5-methyl-piperidin-2-one, (RS,RS,RS)-N-(2-amino-9,10-dimethoxy-1,3,4,6,7,11b-hexahydro-2H-pyrido[2,1-a]isoquinolin-3-yl)-propionamide, (RS,RS,RS)-N-(2-amino-9,10-dimethoxy-1,3,4,6,7,11b-hexahydro-2H-pyrido[2,1-a]isoquinolin-3-yl)-butyramide, cyclopropanecarboxylic acid ((2RS,3RS,11bRS)-2-amino-9,10-dimethoxy-1,3,4,6,7,11b-hexahydro-2H-pyrido [2,1-a]isoquinolin-3-yl)-amide, (SR)-1-((RS,RS,RS)-2-amino-9,10-dimethoxy-1,3,4,6,7,11b-hexahydro-2H-pyrido[2,1-a]isoquinolin-3-yl)-4-fluoromethyl-pyrrolidin-2-one (RS,RS,RS,RS)-1-(2-amino-9,10-dimethoxy-1,3,4,6,7,11b-hexahydro-2H-pyrido[2,1-a]isoquinolin-3-yl)-4-fluoromethyl-pyrrolidin-2-one, (S)-1-((2S,3S,11bS)-2-amino-9,10-dimethoxy-1,3,4,6,7,11b-hexahydro-2H-pyrido [2,1-a]isoquinolin-3-yl)-4-fluoromethyl-pyrrolidin-2-one, (R)-1-((2S,3S,11bS)-2-amino-9,10-dimethoxy-1,3,4,6,7,11b-hexahydro-2H-pyrido [2,1-a]isoquinolin-3-yl)-4-fluoromethyl-pyrrolidin-2-one, (S)-1-((2S,3S,11bS)-2-amino-9,10-dimethoxy-1,3,4,6,7,11b-hexahydro-2H-pyrido [2,1-a]isoquinolin-3-yl)-4-fluoromethyl-pyrrolidin-2-one dihydrochloride, (R)-1-((2S,3S,11bS)-2-amino-9,10-dimethoxy-1,3,4,6,7,11b-hexahydro-2H-pyrido [2,1-a]isoquinolin-3-yl)-4-fluoromethyl-pyrrolidin-2-one dihydrochloride, 3-((RS,RS,RS)-2-amino-9,10-dimethoxy-1,3,4,6,7,11b-hexahydro-2H-pyrido[2,1-a]isoquinolin-3-yl)-oxazolidin-2-one, 3-((2RS,3RS,11bRS)-2-amino-9,10-dimethoxy-1,3,4,6,7,11b-hexahydro-2H-pyrido[2,1-a]isoquinolin-3-yl)-[1,3]oxazinan-2-one, 1-((2RS,3RS,11bRS)-2-amino-9,10-dimethoxy-1,3,4,6,7,11b-hexahydro-2H-pyrido[2,1-a]isoquinolin-3-yl)-5-methyl-pyrrolidin-2-one, 3-((2RS,3RS,11bRS)-2-amino-9,10-dimethoxy-1,3,4,6,7,11b-hexahydro-2H-pyrido[2,1-a]isoquinolin-3-yl)-5-fluoromethyl-oxazolidin-2-one, 1-((2RS,3RS,11bRS)-2-amino-9,10-dimethoxy-1,3,4,6,7,11b-hexahydro-2H-pyrido[2,1-a]isoquinolin-3-yl)-3-methyl-pyrrolidin-2-one, 3-((2RS,3RS,11bRS)-2-amino-9,10-dimethoxy-1,3,4,6,7,11b-hexahydro-2H-pyrido[2,1-a]isoquinolin-3-yl)-5-methyl-oxazolidin-2-one, and pharmaceutically acceptable salts thereof.

Especially preferred compounds of general formula (I) are those selected from the group consisting of:

(RS,RS,RS)-(2-amino-9,10-dimethoxy-1,3,4,6,7,11b-hexahydro-2H-pyrido[2,1-a]isoquinolin-3-yl)-thiazolidin-3-yl-methanone, (−)-(S,S,S)-1-(2-amino-9,10-dimethoxy-1,3,4,6,7,11b-hexahydro-2H-pyrido [2,1-a]isoquinolin-3-yl)-piperidin-2-one, 1-((RS,RS,RS)-2-amino-9,10-dimethoxy-1,3,4,6,7,11b-hexahydro-2H-pyrido [2,1-a]isoquinolin-3-yl)-4-methyl-pyrrolidin-2-one, (RS,RS,RS)-1-(2-amino-9,10-dimethoxy-1,3,4,6,7,11b-hexahydro-2H-pyrido[2,1-a]isoquinolin-3-yl)-5,6-dihydro-1H-pyridin-2-one, (S,S,S)-3-(1,1-dioxo-[1,2]thiazinan-2-yl)-9,10-dimethoxy-1,3,4,6,7,11b-hexahydro-2H-pyrido[2,1-a]isoquinolin-2-ylamine, (R)-1-((S,S,S)-2-amino-9,10-dimethoxy-1,3,4,6,7,11b-hexahydro-2H-pyrido [2,1-a]isoquinolin-3-yl)-4-methyl-pyrrolidin-2-one, (S,S,S)-1-(2-amino-9,10-dimethoxy-1,3,4,6,7,11b-hexahydro-2H-pyrido[2,1-a]isoquinolin-3-yl)-4-methyl-pyrrolidin-2-one, 1-((RS,RS,RS)-2-amino-9,10-dimethoxy-1,3,4,6,7,11b-hexahydro-2H-pyrido[2,1-a]isoquinolin-3-yl)-5-methyl-piperidin-2-one, (S)-1-((2S,3S,11bS)-2-amino-9,10-dimethoxy-1,3,4,6,7,11b-hexahydro-2H-pyrido [2,1-a]isoquinolin-3-yl)-4-fluoromethyl-pyrrolidin-2-one, (R)-1-((2S,3S,11bS)-2-amino-9,10-dimethoxy-1,3,4,6,7,11b-hexahydro-2H-pyrido [2,1-a]isoquinolin-3-yl)-4-fluoromethyl-pyrrolidin-2-one, 3-((2RS,3RS,11bRS)-2-amino-9,10-dimethoxy-1,3,4,6,7,11b-hexahydro-2H-pyrido [2,1-a]isoquinolin-3-yl)-5-methyl-oxazolidin-2-one, and pharmaceutically acceptable salts thereof.

The compounds of formula I have three or more asymmetric carbon atoms and can exist in the form of optically pure enantiomers, mixtures of diastereomers, racemates, or mixtures of diastereoisomeric racemates. The invention embraces all of these forms.

In one preferable embodiment, $R^1$, the amino group in position 2 and the hydrogen in position 11b of the pyrido [2,1-a]isoquinoline backbone are all in S configuration, i.e.

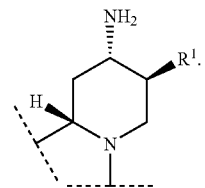

In another preferable embodiment, $R^1$, the amino group in position 2 and the hydrogen in position 11b of the pyrido [2,1-a]isoquinoline backbone are all in R configuration, i.e.

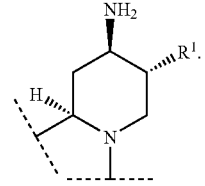

It will be appreciated, that the compounds of general formula (I) in this invention may be derivatised at functional groups to provide derivatives which are capable of conversion back to the parent compound in vivo.

The present invention also relates to a process for the manufacture of compounds of formula I. The compounds of the present invention can be prepared as below:

In the following reaction schemes (Scheme 1 to 6) substituents $R^1$, $R^2$, $R^3$, $R^4$, $R^5$ and $R^6$ have the meanings as defined above, unless otherwise indicated.

Compounds of general formula I are synthesized from carbamate A by methods known in the art, preferably using hydrogen chloride in dioxane or trifluoroacetic acid in dichloromethane when P is Boc. Carbamate A can be obtained from N-benzylcarbamate A' by methods known in the art, preferably by hydrogenation at a pressure of about 3 bar, in the presence of palladium on activated charcoal, in a solvent such as ethanol (Scheme 1).

Scheme 1

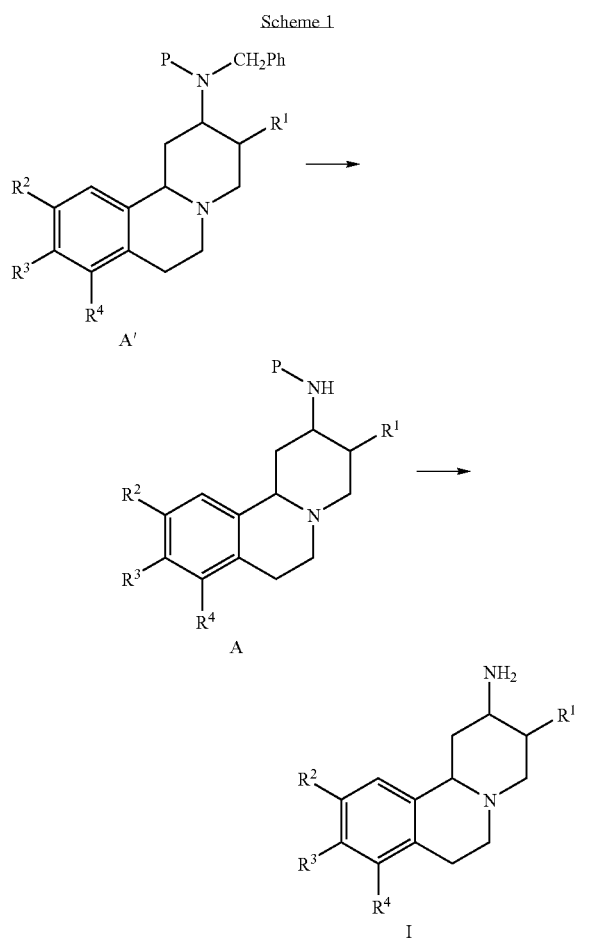

P is a suitable amino protecting group such as benzyloxycarbonyl (Z), allyloxycarbonyl (Aloc), and, preferably, tert-butoxycarbonyl (Boc).

Converting of a compound of formula A into a compound of formula I is done by cleaving the amino protecting group. The cleavage of the amino protecting group can be done by conventional methods as they are for example described in P. Kocienski, Protecting groups, Thieme Verlag Stuttgart New York 1994, pages 192–201. Preferably, cleavage of the amino protecting group is done under acidic conditions. The preferred carbamate amino protecting group is tert-butoxycarbonyl which can be cleaved by acidolysis with strong acids such as hydrogen chloride or trifluoroacetic acid, or with Lewis acids. Preferably, it is cleaved with 4M hydrogen chloride solution in dioxane. Alternatively, the amino protecting group is cleaved by catalytic hydrogenation under conditions well-known to the skilled person.

The synthesis of amide derivatives A1 is outlined in Scheme 2 and starts with the β-ketoester B ($R^a$=methyl or ethyl). Compounds of formula B are well known in the art (e.g., *Helv. Chim. Acta* 1958, 41, 119). Reaction of B with ammonium acetate in a solvent such as methanol produces the β-enamino-ester C, which is reduced, preferably with sodium borohydride/trifluoroacetic acid, to the corresponding β-amino-ester. The amino group is optionally benzylated and then converted to the tert-butyl carbamate of formula D. The ester group of D is hydrolyzed using a base, preferably potassium hydroxide or sodium hydroxide in a water/tetrahydrofuran mixture, to yield the acid E. Compound E is reacted with an appropriate amine in the presence of a suitable coupling agent, e.g., O-(7-azobenzotriazol-1-yl)-1,1,3,3-tetramethyluronium hexafluorophosphate (HATU), and a base, e.g., N-ethyldiisopropylamine, to yield amide A2.

Scheme 2

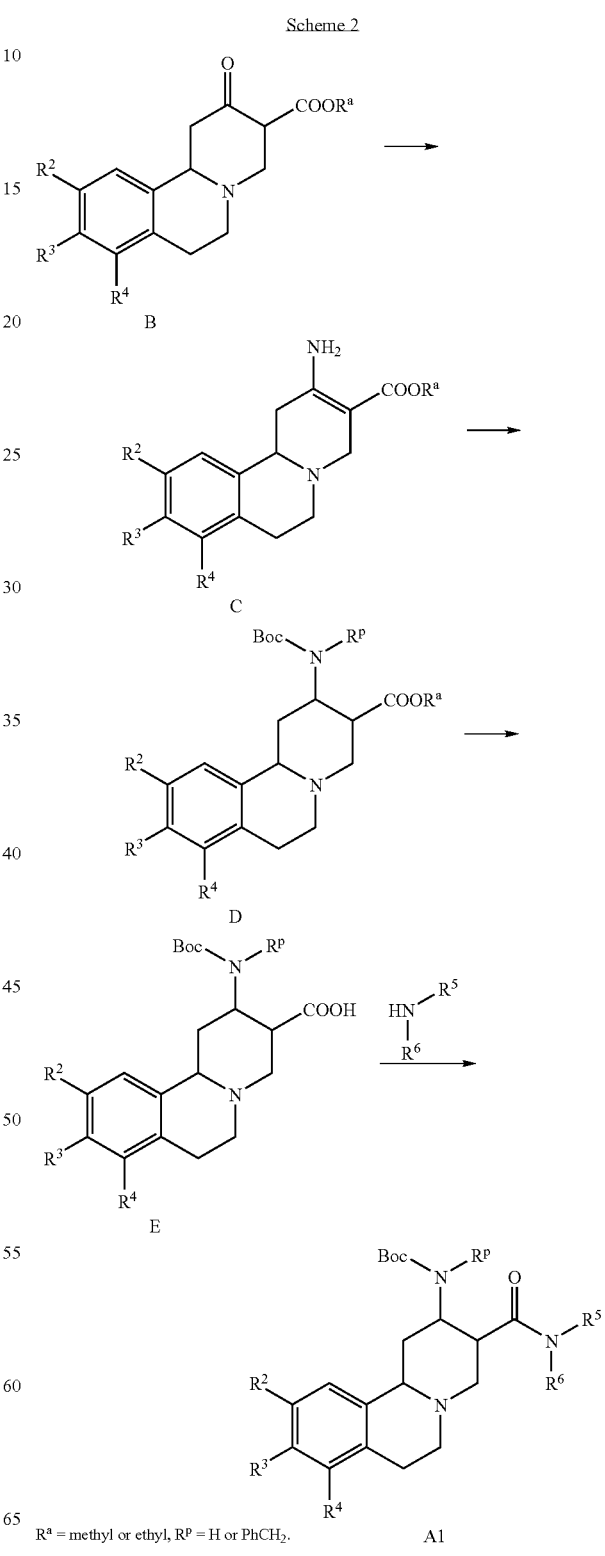

$R^a$ = methyl or ethyl, $R^p$ = H or PhCH$_2$.

The synthesis of lactam or sultam derivatives A2 starts from carboxylic acid E and is outlined in Scheme 3. Acid E is converted into carbamate F through a Curtius rearrangement, using methods known in the art (e.g., *Tetrahedron* 1974, 30, 2157 or *Tetrahedron Lett.* 1984, 25, 3515). Amine G is produced from carbamate F via standard methods (H$_2$, Pd—C, acetic acid in the case of R$^b$=benzyl; Bu$_4$NF/THF, Et$_4$NF/CH$_3$CN, or CsF/DMF in the case of R$^b$=Me$_3$SiCH$_2$CH$_2$). Amine G is reacted with acid chloride, sulfonyl chloride, or chloroformate H in the presence of a base (e.g., triethylamine) to afford amide or sulfonamide K. Alternatively, amide K is obtained from G by reaction with lactone J, followed by conversion of the newly formed hydroxyl into a leaving group, using methods known in the art. Finally, cyclisation of K using a base, e.g., sodium hydride, in a solvent such as N,N-dimethylformamide, optionally in the presence of sodium iodide, leads to A2.

Scheme 3

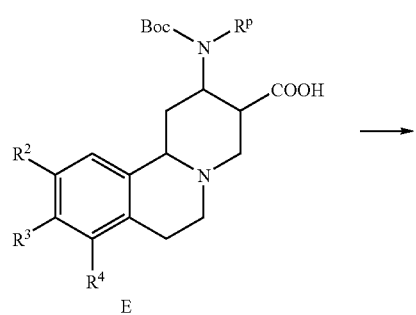

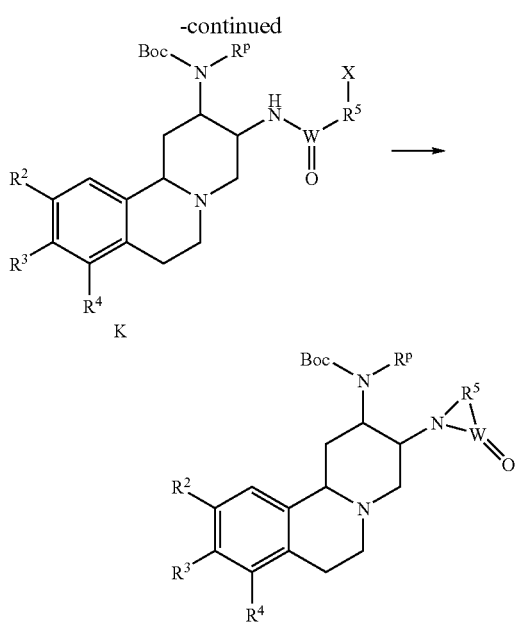

R$^b$ = Me$_3$SiCH$_2$CH$_2$ or PhCH$_2$; R$^p$ = H or PhCH$_2$; W = C or S(=O); X = leaving group, e.g., Cl, Br, or OTs.

Unsaturated lactams of the formula A3 are synthesized from amine G according to Scheme 4. Thus, alkylation of G with alkenyl halide L (in the presence of a base, e.g., triethylamine), followed by acylation (in the presence of a base, e.g., triethylamine) with acyl halide M, affords amide N. Compound N is subjected to ring-closing metathesis (*Acc. Chem. Res.* 2001, 34, 18), using a ruthenium catalyst, e.g., bis(tricyclohexylphosphine)-benzylideneruthenium (IV)dichloride, and optionally a Lewis acid, e.g., tetraisopropyl-orthotitanate, to afford A3.

Scheme 4

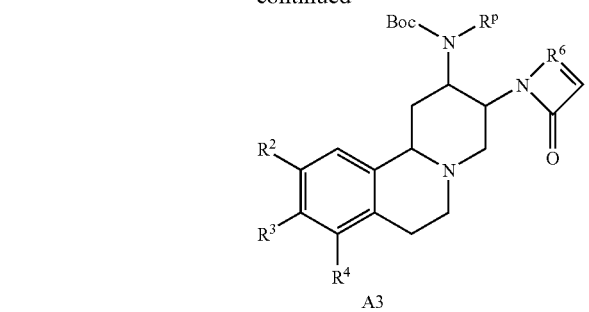

A3

R$^p$ = H or PhCH$_2$; X = leaving group, e.g., Cl or Br.

Amides and sulfonamides of formula A4 are prepared according to Scheme 5, by treatment of amine G (in the case of R$^5$=H) or P (in the case of R$^5$≠H) with appropriate acid chlorides or sulfonyl chlorides. The transformation of G into secondary amine P is performed, e.g., by alkylation, reductive alkylation, or acylation and subsequent reduction, using methods known in the art.

Scheme 5

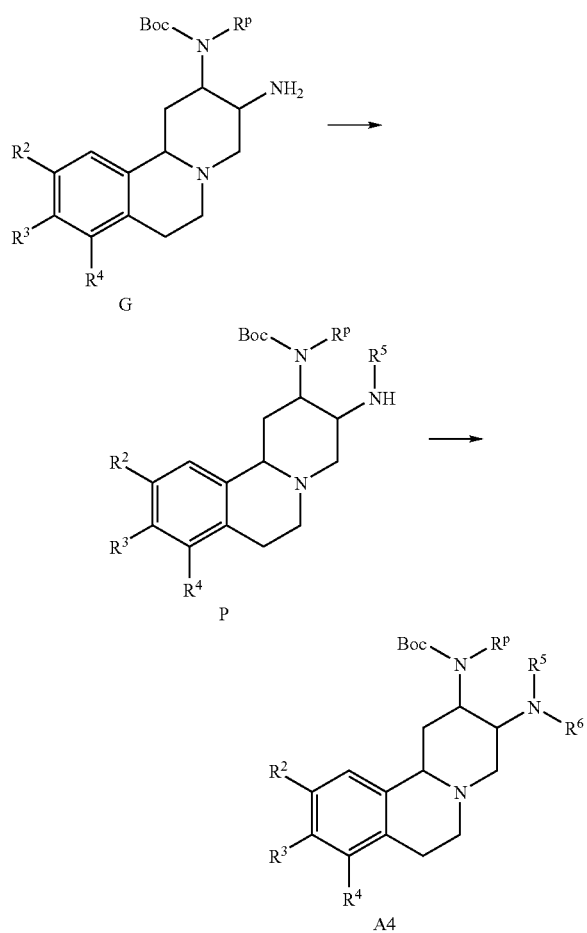

R$^p$ = H or PhCH$_2$.

Ketoester B can be produced from 1,2,3,4-tetrahydro-1-isoquinolineacetate Q via diester intermediate R (Scheme 6), according to literature procedures (e.g., *Helv. Chim. Acta* 1958, 41, 119). Compounds of formula Q are well known in the art and can be produced by a wide variety of methods (e.g., *Synthesis* 1987, 474 and references cited therein).

Scheme 6

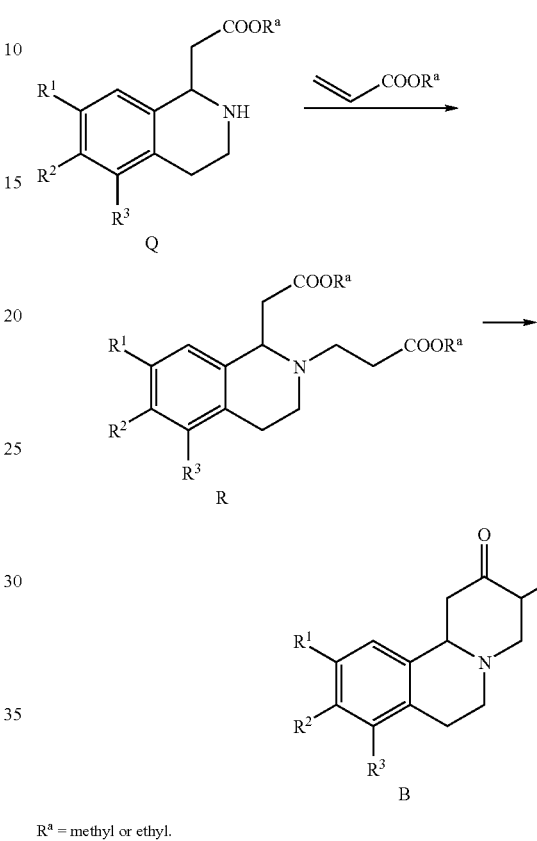

R$^a$ = methyl or ethyl.

The compounds of formula I have three or more asymmetric carbon atoms and can exist in the form of optically pure enantiomers, mixtures of diastereomers, racemates, or mixtures of diastereoisomeric racemates. The optically active forms can be obtained for example by fractional crystallization or asymmetric chromatography (chromatography with a chiral adsorbent or eluant) of the racemates of the compounds of formula I. Likewise, synthetic precursors of the compounds of formula I can be separated into the pure enantiomers. In particular, the optically pure forms of 1,2,3,4-tetrahydro-1-isoquinolineacetate (Q*) can be used as a starting material for the synthesis of optically pure compounds of formula I. Optically pure forms of Q are well known in the literature and can be produced from the racemates by fractional crystallization using chiral resolving agents, e.g., tartranilic acids, as described by Montzka et al. (U.S. Pat. No. 3,452,086). Alternatively, the pure enantiomers Q* can be synthesized from achiral precursors, e.g., by addition of ketene silyl acetals S to nitrones of formula T in the presence of chiral Lewis acids, followed by reduction of the intermediate U with zinc, as described by Murahashi and co-workers (*J. Am. Chem. Soc.* 2002, 124, 2888, Scheme 7).

Scheme 7

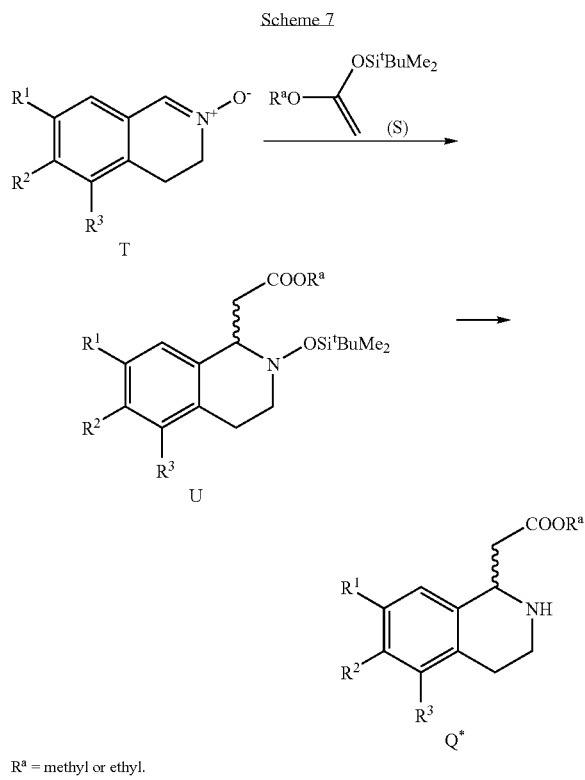

$R^a$ = methyl or ethyl.

The invention further relates to compounds of formula (I) as defined above, when manufactured according to a process as defined above.

As described above, the compounds of formula (I) of the present invention can be used as medicaments for the treatment and/or prophylaxis of diseases which are associated with DPP-IV such as diabetes, particularly non-insulin dependent diabetes mellitus, impaired glucose tolerance, inflammatory bowel disease, Colitis Ulcerosa, Morbus Crohn, obesity, and/or metabolic syndrome or β-cell protection, preferably non-insulin dependent diabetes mellitus and/or impaired glucose tolerance. Furthermore, the compounds of the present invention can be used as diuretic agents or for the treatment and/or prophylaxis of hypertension.

The invention therefore also relates to pharmaceutical compositions comprising a compound as defined above and a pharmaceutically acceptable carrier and/or adjuvant.

Further, the invention relates to compounds as defined above for use as therapeutic active substances, particularly as therapeutic active substances for the treatment and/or prophylaxis of diseases which are associated with DPP-IV such as diabetes, particularly non-insulin dependent diabetes mellitus, impaired glucose tolerance, inflammatory bowel disease, Colitis Ulcerosa, Morbus Crohn, obesity, and/or metabolic syndrome or β-cell protection, preferably for use as therapeutic active substances for the treatment and/or prophylaxis of non-insulin dependent diabetes mellitus and/or impaired glucose tolerance. Furthermore, the invention relates to compounds as defined above for use as diuretic agents or for use as therapeutic active substances for the treatment and/or prophylaxis of hypertension.

In another embodiment, the invention relates to a method for the treatment and/or prophylaxis of diseases which are associated with DPP-IV such as diabetes, particularly non-insulin dependent diabetes mellitus, impaired glucose tolerance, inflammatory bowel disease, Colitis Ulcerosa, Morbus Crohn, obesity, and/or metabolic syndrome or β-cell protection, preferably for the treatment and/or prophylaxis of non-insulin dependent diabetes mellitus and/or impaired glucose tolerance, which method comprises administering a compound as defined above to a human being or animal. Furthermore, the invention relates to a method for the treatment and/or prophylaxis as defined above, wherein the disease is hypertension or wherein a diuretic agent has a beneficial effect. The invention further relates to the use of compounds as defined above for the treatment and/or prophylaxis of diseases which are associated with DPP-IV such as diabetes, particularly non-insulin dependent diabetes mellitus, impaired glucose tolerance, inflammatory bowel disease, Colitis Ulcerosa, Morbus Crohn, obesity, and/or metabolic syndrome or β-cell protection, preferably for the treatment and/or prophylaxis of non-insulin dependent diabetes mellitus and/or impaired glucose tolerance. Furthermore, the invention relates to the use as defined above, wherein the disease is hypertension or to the use as diuretic agent.

In addition, the invention relates to the use of compounds as defined above for the preparation of medicaments for the treatment and/or prophylaxis of diseases which are associated with DPP-IV such as diabetes, particularly non-insulin dependent diabetes mellitus, impaired glucose tolerance, inflammatory bowel disease, Colitis Ulcerosa, Morbus Crohn, obesity, and/or metabolic syndrome or β-cell protection, preferably for the treatment and/or prophylaxis of non-insulin dependent diabetes mellitus and/or impaired glucose tolerance. Such medicaments comprise a compound as defined above. Furthermore, the invention relates to the use as defined above, wherein the disease is hypertension or the use for the preparation of diuretic agents.

In context with the methods and uses defined above, the following diseases relate to a preferred embodiment: diabetes, particularly non-insulin dependent diabetes mellitus, impaired glucose tolerance, obesity, and/or metabolic syndrome or β-cell protection, preferably non-insulin dependent diabetes mellitus and/or impaired glucose tolerance.

The compounds of formula (I) can be manufactured by the methods given below, by the methods given in the Examples or by analogous methods. Appropriate reaction conditions for the individual reaction steps are known to the person skilled in the art. Starting materials are either commercially available or can be prepared by methods analogous to the methods given below or in the Examples or by methods known in the art.

The following tests were carried out in order to determine the activity of the compounds of formula I.

Activity of DPP-IV inhibitors are tested with natural human DPP-IV derived from a human plasma pool or with recombinat human DPP-IV. Human citrate plasma from different donors is pooled, filterted through a 0.2 micron membrane under sterile conditions and aliquots of 1 ml are shock frozen and stored at −120° C. until used. In the colorimetric DPP-IV assay 5 to 10 μl human plasma and in the fluorometric assay 1.0 μl of human plasma in a total assay volume of 100 μl is used as an enzyme source. The cDNA of the human DPP-IV sequence of amino acid 31- to 766, restricted for the N-terminus and the transmembrane domain, is cloned into *Pichia pastoris*. Human DPP-IV is expressed and purified from the culture medium using conventional column chromatography including size exclusion and anion and cation chromatography. The purity of the final enzyme preparation of Coomassie blue SDS-PAGE is >95%. In the calorimetric DPP-IV assay 20 ng rec.-h DPP-IV and in the fluorometric assay 2 ng rec-h DPP-IV in a total assay volume of 100 µl is used as an enzyme source.

In the fluorogenic assay Ala-Pro-7-amido-4-trifluoromethylcoumarin (Calbiochem No 125510) is used as a substrate. A 20 mM stock solution in 10% DMF/H$_2$O is stored at −20° C. until use. In IC$_{50}$ determinations a final substrate concentration of 50 µM is used. In assays to determine kinetic parameters as K$_m$, V$_{max}$, K$_i$, the substrate concentration is varied between 10 µM and 500 µM.

In the colorimetric assay H-Ala-Pro-pNA.HCl (Bachem L-1115) is used as a substrate. A 10 mM stock solution in 10% MeOH/H$_2$O is stored at −20° C. until use. In IC$_{50}$ determinations a final substrate concentration of 200 µM is used. In assays to determine kinetic parameters as K$_m$, V$_{max}$, K$_i$, the substrate concentration is varied between 100 µM and 2000 µM. Fluorescence is detected in a Perkin Elmer Luminescence Spectrometer LS 50B at an excitation wavelength of 400 nm and an emission wavelength of 505 nm continuously every 15 seconds for 10 to 30 minutes. Initial rate constants are calculated by best fit linear regression.

The absorption of pNA liberated from the colorimetric substrate is detected in a Packard SpectraCount at 405 nm continuosly every 2 minutes for 30 to 120 minutes. Initial rate constants are calculated by best fit linear regression.

DPP-IV activity assays are performed in 96 well plates at 37° C. in a total assay volume of 100 µl. The assay buffer consists of 50 mM Tris/HCl pH 7.8 containing 0.1 mg/ml BSA and 100 mM NaCl. Test compounds are solved in 100% DMSO, diluted to the desired concentration in 10% DMSO/H$_2$O. The final DMSO concentration in the assay is 1% (v/v). At this concentration enzyme inactivation by DMSO is <5%. Compounds are with (10 minutes at 37° C.) and without preincubation with the enzyme. Enzyme reactions are started with substrate application followed by immediate mixing.

IC$_{50}$ determinations of test compounds are calculated by non-linear best fit regression of the DPP-IV inhibition of at least 5 different compound concentrations. Kinetic parameters of the enzyme reaction are calculated at at least 5 different substrate concentrations and at least 5 different test compound concentrations.

The compounds of the present invention exhibit IC$_{50}$ values of 0.1 nM to 10 µM, more preferably of 0.1–100 nM, as shown in the following table:

| Example | IC$_{50}$ [µM] |
|---------|---------|
| 2 | 0.041 |
| 6 | 0.023 |
| 10 | 0.0093 |
| 12 | 0.033 |
| 16 | 0.131 |

The compounds of formula I and/or their pharmaceutically acceptable salts can be used as medicaments, e.g. in the form of pharmaceutical preparations for enteral, parenteral or tropical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 100 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1–500 mg, preferably 1–100 mg, of a compound of formula I.

The following Examples serve to illustrate the present invention in more detail. They are, however, not intended to limit its scope in any manner.

EXAMPLES

Abbreviations: MS=mass spectrometry, aq.=aqueous, r.t.=room temperature, THF=tetrahydrofuran, NMR=nuclear magnetic resonance spectroscopy, DMF=dimethylformamide, DMSO=dimethylsulfoxide, ISP=ionspray.

Example 1

(RS,RS,RS)-(2-Amino-9,10-dimethoxy-1,3,4,6,7,11b-hexahydro-2H-pyrido[2,1-a]isoquinolin-3-yl)-pyrrolidin-1-yl-methanone

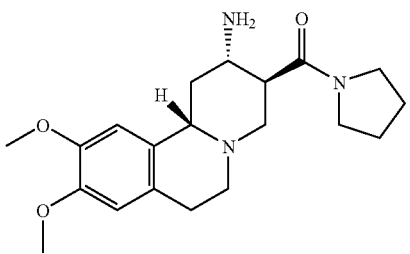

a) 2-Amino-9,10-dimethoxy-1,6,7,11b-tetrahydro-4H-pyrido[2,1-a]isoquinoline-3-carboxylic acid ethyl ester A mixture of 9,10-dimethoxy-2-oxo-1,3,4,6,7,11b-hexahydro-2H-pyrido[2,1-a]isoquinoline-3-carboxylic acid ethyl ester (*Helv. Chim. Acta* 1958, 41, 119; 4.00 g, 12.0 mmol) and ammonium acetate (13.9 g, 180 mmol) in methanol was stirred 5 h at room temperature. After evaporation of the solvent the residue was partitioned between dichloromethane and 1 M aq. sodium hydroxide solution. The organic layer was dried (MgSO₄), and triturated with heptane to afford the title compound (3.71 g, 93%). Off-white solid, MS (ISP) 333.2 (M+H)⁺.

b) (RS,RS,RS)-2-tert-Butoxycarbonylamino-9,10-dimethoxy-1,3,4,6,7,11b-hexahydro-2H-pyrido [2,1-a]isoquinoline-3-carboxylic acid ethyl ester Trifluoroacetic acid (120 mL) was added at 0° C. to a solution of 2-amino-9,10-dimethoxy-1,6,7,11b-tetrahydro-4H-pyrido[2,1-a]isoquinoline-3-carboxylic acid ethyl ester (6.90 g, 20.8 mmol) in tetrahydrofuran (60 mL), then after 30 min the homogeneous solution was treated with sodium borohydride (1.64 g, 41.5 mmol) and stirred for another 40 min. The reaction mixture was concentrated in vacuo and the residue partitioned between 2 M aq. sodium hydroxide solution and dichloromethane. The organic layer was washed with brine, dried (MgSO₄) and evaporated. The residue was dissolved in dichloromethane (80 mL), and a solution of di-tert-butyl-dicarbonate (4.98 g, 22.8 mmol) in dichloromethane (50 mL) was added at r.t. The solution was stirred overnight at r.t., concentrated, and the residue was triturated in heptane to afford the title compound (7.44 g, 83%). Light yellow solid, MS (ISP) 435.4 (M+H)⁺.

c) (RS,RS,RS)-2-tert-Butoxycarbonylamino-9,10-dimethoxy-1,3,4,6,7,11b-hexahydro-2H-pyrido [2,1-a]isoquinoline-3-carboxylic acid Potassium hydroxide pellets (86%, 4.47 g, 68.5 mmol) was added to a suspension of (RS,RS,RS)-2-tert-butoxycarbonylamino-9,10-dimethoxy-1,3,4,6,7,11b-hexahydro-2H-pyrido[2,1-a]isoquinoline-3-carboxylic acid ethyl ester (7.44 g, 17.1 mmol) in tetrahydrofuran/water 1:1 (140 mL). After heating 5 h at reflux, the mixture was concentrated in vacuo. The residue was taken up in 1M aq. potassium phosphate buffer (pH 6.85) and dichloromethane, and ethanol was added until a clear two-phase mixture was obtained. The organic layer was separated, washed with brine and evaporated to afford the title compound (6.91 g, 99%). Light yellow solid, MS (ISP) 405.3 (M−H)⁻.

d) (RS,RS,RS)-[9,10-Dimethoxy-3-(pyrrolidine-1-carbonyl)-1,3,4,6,7,11b-hexahydro-2H-pyrido[2,1-a]isoquinolin-2-yl]-carbamic acid tert-butyl ester N-Ethyldiisopropylamine (96 mg, 0.74 mmol) and O-(7-Azabenzotriazol-1-yl)-N,N,N',N'-tetramethyluronium hexafluorophosphate (HATU, 103 mg, 0.27 mmol) were added at r.t. to a suspension of (RS,RS,RS)-2-tert-butoxycarbonylamino-9,10-dimethoxy-1,3,4,6,7,11b-hexahydro-2H-pyrido[2,1-a]isoquinoline-3-carboxylic acid (100 mg, 0.25 mmol) in N,N,dimethylformamide (2 mL), then after 45 min pyrrolidine (19 mg, 0.27 mmol) was added. The homogeneous solution was stirred 90 min at r.t., then partitioned between hexane/ethyl acetate 1:1 and water. The organic layer was washed with brine, dried (MgSO₄), and evaporated, and the residue chromatographed (SiO₂, CH₂Cl₂/MeOH/NH₄OH 80:1:0.2) to produce the title compound (58 mg, 51%). Light yellow solid, MS (ISP) 460.5 (M+H)⁺.

e) (RS,RS,RS)-(2-Amino-9,10-dimethoxy-1,3,4,6,7,11b-hexahydro-2H-pyrido [2,1-a]isoquinolin-3-yl)-pyrrolidin-1-yl-methanone A solution of (RS,RS,RS)-[9,10-dimethoxy-3-(pyrrolidine-1-carbonyl)-1,3,4,6,7,11b-hexahydro-2H-pyrido [2,1-a]isoquinolin-2-yl]-carbamic acid tert-butyl ester (55 mg, 0.12 mmol) in hydrogen chloride solution (4 M in dioxane, 1 mL) was stirred 1 h at r.t., then neutralized with CH₂Cl₂/MeOH/NH₄OH 90:10:0.25 and evaporated. Chromatography of the residue (SiO₂, CH₂Cl₂/MeOH/NH₄OH 90:10:0.25) afforded the title compound (32 mg, 74%). Off-white foam, MS (ISP) 359.6 (M⁺).

Example 2

(RS,RS,RS)-(2-Amino-9,10-dimethoxy-1,3,4,6,7,11b-hexahydro-2H-pyrido[2,1-a]isoquinolin-3-yl)-thiazolidin-3-yl-methanone

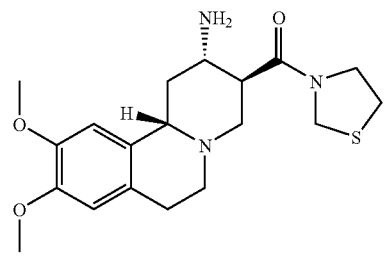

a) (RS,RS,RS)-[9,10-Dimethoxy-3-(thiazolidine-3-carbonyl)-1,3,4,6,7,11b-hexahydro-2H-pyrido[2,1-a]isoquinolin-2-yl]-carbamic acid tert-butyl ester The title compound was produced in accordance with the general method of Example 1d from (RS,RS,RS)-2-tert-butoxycarbonylamino-9,10-dimethoxy-1,3,4,6,7,11b-hexahydro-2H-pyrido [2,1-a]isoquinoline-3-carboxylic acid (Example 1c) and thiazolidine. Off-white solid, MS (ISP) 478.3 (M+H)⁺.

b) (RS,RS,RS)-(2-Amino-9,10-dimethoxy-1,3,4,6,7,11b-hexahydro-2H-pyrido [2,1-a]isoquinolin-3-yl)-thiazolidin-3-yl-methanone The title compound was produced in accordance with the general method of Example 1e from (RS,RS,RS)-[9,10-dimethoxy-3-(thiazolidine-3-carbonyl)-1,3,4,6,7,11b- hexahydro-2H-pyrido[2,1-a]isoquinolin-2-yl]-carbamic acid tert-butyl ester. White foam, MS (ISP) 378.3 (M+H)+.

Example 3

(RS,RS,RS)-(2-Amino-9,10-dimethoxy-1,3,4,6,7,11b-hexahydro-2H-pyrido[2,1-a]isoquinolin-3-yl)-azetidin-1-yl-methanone

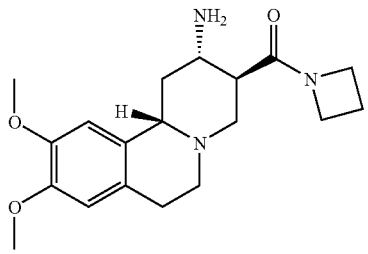

a) (RS,RS,RS)-[3-(Azetidine-1-carbonyl)-9,10-dimethoxy-1,3,4,6,7,11b-hexahydro-2H-pyrido [2,1-a]isoquinolin-2-yl]-carbamic acid tert-butyl ester The title compound was produced in accordance with the general method of Example 1d from (RS,RS,RS)-2-tert-butoxycarbonylamino-9,10-dimethoxy-1,3,4,6,7,11b-hexahydro-2H-pyrido [2,1-a]isoquinoline-3-carboxylic acid (Example 1c) and azetidine. Light yellow solid, MS (ISP) 446.3 (M+H)+.

b) (RS,RS,RS)-(2-Amino-9,10-dimethoxy-1,3,4,6,7,11b-hexahydro-2H-pyrido[2,1-a]isoquinolin-3-yl)-azetidin-1-yl-methanone.

The title compound was produced in accordance with the general method of Example 1e from (RS,RS,RS)-[3-(azetidine-1-carbonyl)-9,10-dimethoxy-1,3,4,6,7,11b-hexahydro-2H-pyrido[2,1-a]isoquinolin-2-yl]-carbamic acid tert-butyl ester. White foam, MS (ISP) 346.2 (M+H)+.

Example 4

(SS)-1-((RS,RS,RS)-2-Amino-9,10-dimethoxy-1,3,4,6,7,11b-hexahydro-2H-pyrido[2,1-a]isoquinoline-3-carbonyl)-pyrrolidine-2-carbonitrile

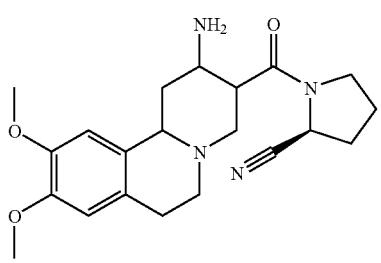

a) [(RS,RS,RS)-3-((SS)-2-Cyano-pyrrolidine-1-carbonyl)-9,10-dimethoxy-1,3,4,6,7,11b-hexahydro-2H-pyrido [2,1-a]isoquinolin-2-yl]-carbamic acid tert-butyl ester The title compound was prepared in accordance with the general method of Example 1d from (RS,RS,RS)-2-tert-butoxycarbonylamino-9,10-dimethoxy-1,3,4,6,7,11b-hexahydro-2H-pyrido[2,1-a]isoquinoline-3-carboxylic acid (Example 1c) and (S)-2-cyano-pyrrolidine (EP1258476). Yellow solid, MS (ISP) 485.5 (M+H)+.

b) (S)-1-((RS,RS,RS)-2-Amino-9,10-dimethoxy-1,3,4,6,7,11b-hexahydro-2H-pyrido[2,1-a]isoquinoline-3-carbonyl)-pyrrolidine-2-carbonitrile The title compound was prepared in accordance with the general method of Example 1e from [(RS,RS,RS)-3-((SS)-2-cyano-pyrrolidine-1-carbonyl)-9,10-dimethoxy-1,3,4,6,7,11b-hexahydro-2H-pyrido[2,1-a]isoquinolin-2-yl]-carbamic acid tert-butyl ester. Light yellow solid, MS (ISP) 385.2 (M+H)+.

Example 5

1-((RS,RS,RS)-2-Amino-9,10-dimethoxy-1,3,4,6,7,11b-hexahydro-2H-pyrido [2,1-a]isoquinolin-3-yl)-piperidin-2-one

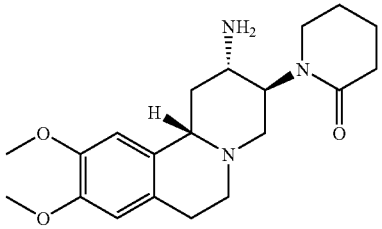

a) (RS,RS,RS)-(2-tert-Butoxycarbonylamino-9,10-dimethoxy-1,3,4,6,7,11b-hexahydro-2H-pyrido [2,1-a]isoquinolin-3-yl)-carbamic acid 2-trimethylsilanyl-ethyl ester A mixture of (RS,RS,RS)-2-tert-butoxycarbonylamino-9,10-dimethoxy-1,3,4,6,7,11b-hexahydro-2H-pyrido[2,1-a]isoquinoline-3-carboxylic acid (Example 1c, 6.91 g, 17.0 mmol), diphenylphosphoryl azide (7.40 g, 25.6 mmol), triethylamine (1.72 g, 17.0 mmol), 2-(trimethylsilyl)-ethanol (30.2 g, 256 mmol) and toluene (40 mL) was heated 48 h at 80° C. under a gentle nitrogen stream. The reaction mixture was then concentrated in vacuo, the residue chromatographed (SiO$_2$, CH$_2$Cl$_2$/MeOH/NH$_4$OH 80:1:0.2), and the product fractions triturated in hexane/ethyl acetate 1:1 to afford the title compound (5.22 g, 59%). White solid, MS (ISP) 522.4 (M+H)+.

b) (RS,RS,RS)-(3-Amino-9,10-dimethoxy-1,3,4,6,7,11b-hexahydro-2H-pyrido [2,1-a]isoquinolin-2-yl)-carbamic acid tert-butyl ester A suspension of (RS,RS,RS)-(2-tert-butoxycarbonylamino-9,10-dimethoxy-1,3,4,6,7,11b-hexahydro-2H-pyrido[2,1-a]isoquinolin-3-yl)-carbamic acid 2-trimethylsilanyl-ethyl ester (5.22 g, 10.0 mmol) in tetrabutylammonium fluoride solution (1 M in THF, 42 mL, 42 mmol) was heated 90 min at 50° C. The resultant solution was concentrated in vacuo and chromatographed (CH$_2$Cl$_2$/MeOH/NH$_4$OH 95:5:0.25) to afford the title compound (3.59 g, 95%). Light yellow solid, MS (ISP) 378.4 (M+H)⁺; $t_R$=7.2 and 18.9 min (Chiralpak® AD 25×0.03 cm, heptane/ethanol/triethylamine 70:30:0.3, flow rate 4 μL/min).

c) (RS,RS,RS)-[3-(5-Chloro-pentanoylamino)-9,10-dimethoxy-1,3,4,6,7,11b-hexahydro-2H-pyrido[2,1-a]isoquinolin-2-yl]-carbamic acid tert-butyl ester 5-Chlorovaleryl chloride (466 mg, 2.91 mmol) was added at a 0° C. to a solution of (RS,RS,RS)-(3-amino-9,10-dimethoxy-1,3,4,6,7,11b-hexahydro-2H-pyrido[2,1-a]isoquinolin-2-yl)-carbamic acid tert-butyl ester (1.00 g, 2.65 mmol) and triethylamine (295 mg, 2.91 mmol), and the resultant suspension was allowed to reach r.t. over 30 min. The reaction mixture was then partitioned between dichloromethane and water, the organic layer was washed with brine, dried (MgSO₄), and evaporated. Chromatography of the residue (SiO₂, CH₂Cl₂/MeOH/NH₄OH 80:2:0.2) afforded the title compound (1.23 g, 94%). White solid, MS (ISP) 496.3 (M+H)⁺.

d) (RS,RS,RS)-[9,10-Dimethoxy-3-(2-oxo-piperidin-1-yl)-1,3,4,6,7,11b-hexahydro-2H-pyrido[2,1-a]isoquinolin-2-yl]-carbamic acid tert-butyl ester A solution of (RS,RS,RS)-[3-(5-chloro-pentanoylamino)-9,10-dimethoxy-1,3,4,6,7,11b-hexahydro-2H-pyrido [2,1-a]isoquinolin-2-yl]-carbamic acid tert-butyl ester (1.22 g, 2.46 mmol) in N,N-dimethylformamide (18 mL) was treated with sodium iodide (369 mg, 2.46 mmol) and sodium hydride (60% dispersion in oil, 197 mg, 4.92 mmol) and stirred 2 h at r.t., then poured onto ice and partitioned between heptane/ethyl acetate 1:1 and water. The organic layer was washed with brine, dried (MgSO₄), and evaporated. Chromatography of the residue (SiO₂, CH₂Cl₂/MeOH/NH₄OH 80:2:0.2) afforded the title compound (769 mg, 68%). White solid, MS (ISP) 460.3 (M+H)⁺.

e) 1-((RS,RS,RS)-2-Amino-9,10-dimethoxy-1,3,4,6,7,11b-hexahydro-2H-pyrido [2,1-a]isoquinolin-3-yl)-piperidin-2-one The title compound was prepared in accordance with the general method of Example 1e from (RS,RS,RS)-[9,10-dimethoxy-3-(2-oxo-piperidin-1-yl)-1,3,4,6,7,11b-hexahydro-2H-pyrido[2,1-a]isoquinolin-2-yl]-carbamic acid tert-butyl ester. White solid, MS (ISP) 360.3 (M+H)⁺.

Examples 6 and 7

(−)-(S,S,S)-1-(2-Amino-9,10-dimethoxy-1,3,4,6,7,11b-hexahydro-2H-pyrido[2,1-a]isoquinolin-3-yl)-piperidin-2-one

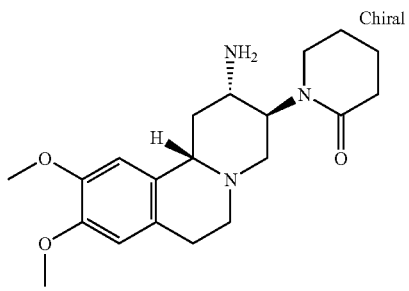

and (+)-(R,R,R)-1-(2-Amino-9,10-dimethoxy-1,3,4,6,7,11b-hexahydro-2H-pyrido [2,1-a]isoquinolin-3-yl)-piperidin-2-one

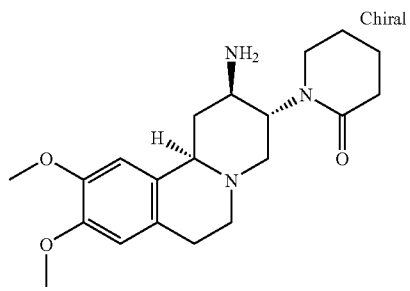

(RS,RS,RS)-[9,10-Dimethoxy-3-(2-oxo-piperidin-1-yl)-1,3,4,6,7,11b-hexahydro-2H-pyrido[2,1-a]isoquinolin-2-yl]-carbamic acid tert-butyl ester (580 mg, 1.61 mmol) was dissolved in ethanol/heptane 3:2 (5 mL) and subjected to preparative HPLC (Chiralpak® AD column, heptane/ethanol 80:20).

(−)-(S,S,S)-1-(2-Amino-9,10-dimethoxy-1,3,4,6,7,11b-hexahydro-2H-pyrido[2,1-a]isoquinolin-3-yl)-piperidin-2-one: Light yellow semisolid, 220 mg (38%), $t_R$=32.0 min (Chiralpak® AD 25×0.46 cm, heptane/ethanol 80:20, flow rate 1 mL/min). (+)-(R,R,R)-1-(2-Amino-9,10-dimethoxy-1,3,4,6,7,11b-hexahydro-2H-pyrido [2,1-a]isoquinolin-3-yl)-piperidin-2-one: Light yellow semisolid, 207 mg (36%), $t_R$=55.4 min (Chiralpak® AD 25×0.46 cm, heptane/ethanol 80:20, flow rate 1 mL/min).

Example 8

1-((RS,RS,RS)-2-Amino-9,10-dimethoxy-1,3,4,6,7,11b-hexahydro-2H-pyrido [2,1-a]isoquinolin-3-yl)-4-methyl-piperidin-2-one

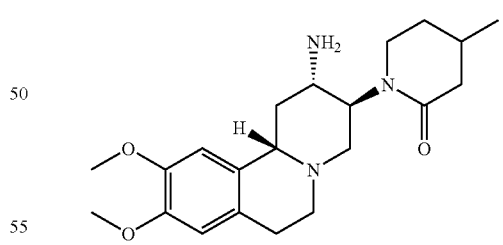

a) (RS,RS,RS)-[3-(5-Chloro-3-methyl-pentanoylamino)-9,10-dimethoxy-1,3,4,6,7,11b-hexahydro-2H-pyrido[2,1-a]isoquinolin-2-yl]-carbamic acid tert-butyl ester The title compound was produced in accordance with the general method of Example 5c from (RS,RS,RS)-(3-amino-9,10-dimethoxy-1,3,4,6,7,11b-hexahydro-2H-pyrido[2,1-a]isoquinolin-2-yl)-carbamic acid tert-butyl ester (Example 5b) and 5-chloro-3-methylvaleryl chloride (DE2621576). White solid, MS (ISP) 510.4 (M+H)⁺.

b) (RS,RS,RS)-[9,10-Dimethoxy-3-(4-methyl-2-oxo-piperidin-1-yl)-1,3,4,6,7,11b-hexahydro-2H-pyrido[2,1-a]isoquinolin-2-yl]-carbamic acid tert-butyl ester The title compound was produced in accordance with the general method of Example 5d from (RS,RS,RS)-[3-(5-chloro-3-methyl-pentanoylamino)-9,10-dimethoxy-1,3,4,6,7,11b-hexahydro-2H-pyrido [2,1-a]isoquinolin-2-yl]-carbamic acid tert-butyl ester. Light yellow solid, MS (ISP) 474.3 (M+H)+.

c) 1-((RS,RS,RS)-2-Amino-9,10-dimethoxy-1,3,4,6,7,11b-hexahydro-2H-pyrido [2,1-a]isoquinolin-3-yl)-4-methyl-piperidin-2-one The title compound was produced in accordance with the general method of Example 1e from (RS,RS,RS)-[9,10-dimethoxy-3-(4-methyl-2-oxo-piperidin-1-yl)-1,3,4,6,7,11b-hexahydro-2H-pyrido[2,1-a]isoquinolin-2-yl]-carbamic acid tert-butyl ester. White solid, MS (ISP) 374.2 (M+H)+.

Example 9

(RS,RS,RS)-1-(2-Amino-9,10-dimethoxy-1,3,4,6,7,11b-hexahydro-2H-pyrido [2,1-a]isoquinolin-3-yl)-pyrrolidin-2-one

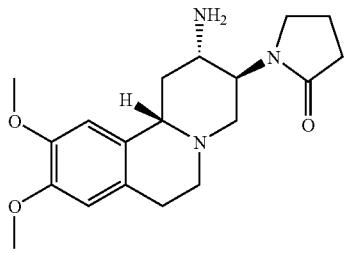

a) (RS,RS,RS)-[3-(4-Chloro-butyrylamino)-9,10-dimethoxy-1,3,4,6,7,11b-hexahydro-2H-pyrido[2,1-a]isoquinolin-2-yl]-carbamic acid tert-butyl ester The title compound was produced in accordance with the general method of Example 5c from (RS,RS,RS)-(3-amino-9,10-dimethoxy-1,3,4,6,7,11b-hexahydro-2H-pyrido[2,1-a]isoquinolin-2-yl)-carbamic acid tert-butyl ester (Example 5b) and 4-chlorobutyryl chloride. White solid, MS (ISP) 482.4 (M+H)+.

b) (RS,RS,RS)-[9,10-Dimethoxy-3-(2-oxo-pyrrolidin-1-yl)-1,3,4,6,7,11b-hexahydro-2H-pyrido [2,1-a]isoquinolin-2-yl]-carbamic acid tert-butyl ester The title compound was produced in accordance with the general method of Example 5d from (RS,RS,RS)-[3-(4-chloro-butyrylamino)-9,10-dimethoxy-1,3,4,6,7,11b-hexahydro-2H-pyrido[2,1-a]isoquinolin-2-yl]-carbamic acid tert-butyl ester. Light yellow solid, MS (ISP) 446.3 (M+H)+.

c) (RS,RS,RS)-[3-(4-Chloro-butyrylamino)-9,10-dimethoxy-1,3,4,6,7,11b-hexahydro-2H-pyrido [2,1-a]isoquinolin-2-yl]-carbamic acid tert-butyl ester The title compound was produced in accordance with the general method of Example 1e from (RS,RS,RS)-[9,10-dimethoxy-3-(2-oxo-pyrrolidin-1-yl)-1,3,4,6,7,11b-hexahydro-2H-pyrido [2,1-a]isoquinolin-2-yl]-carbamic acid tert-butyl ester. White solid, MS (ISP) 346.2 (M+H)+.

Example 10

1-((RS,RS,RS)-2-Amino-9,10-dimethoxy-1,3,4,6,7,11b-hexahydro-2H-pyrido[2,1-a]isoquinolin-3-yl)-4-methyl-pyrrolidin-2-one

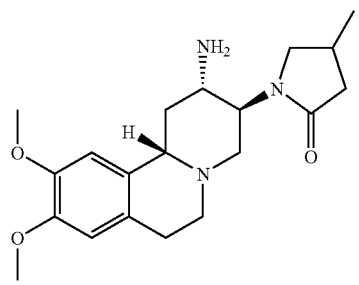

a) [(RS,RS,RS)-3-(4-Chloro-3-methyl-butyrylamino)-9,10-dimethoxy-1,3,4,6,7,11b-hexahydro-2H-pyrido[2,1-a]isoquinolin-2-yl]-carbamic acid tert-butyl ester The title compound was produced in accordance with the general method of Example 5c from (RS,RS,RS)-(3-amino-9,10-dimethoxy-1,3,4,6,7,11b-hexahydro-2H-pyrido [2,1-a] isoquinolin-2-yl)-carbamic acid tert-butyl ester (Example 5b) and 4-chloro-3-methylbutyryl chloride (Chem. Ber. 1964, 97, 2544). White solid, MS (ISP) 496.3 (M+H)+.

b) [(RS,RS,RS)-9,10-Dimethoxy-3-(4-methyl-2-oxo-pyrrolidin-1-yl)-1,3,4,6,7,11b-hexahydro-2H-pyrido[2,1-a]isoquinolin-2-yl]-carbamic acid tert-butyl ester The title compound was produced in accordance with the general method of Example 5d from [(RS,RS,RS)-3-(4-chloro-3-methyl-butyrylamino)-9,10-dimethoxy-1,3,4,6,7,11b-hexahydro-2H-pyrido[2,1-a]isoquinolin-2-yl]-carbamic acid tert-butyl ester. Light yellow solid, MS (ISP) 460.3 (M+H)+.

c) 1-((RS,RS,RS)-2-Amino-9,10-dimethoxy-1,3,4,6,7,11b-hexahydro-2H-pyrido [2,1-a]isoquinolin-3-yl)-4-methyl-pyrrolidin-2-one The title compound was produced in accordance with the general method of Example 1e from [(RS,RS,RS)-9,10-dimethoxy-3-(4-methyl-2-oxo-pyrrolidin-1-yl)-1,3,4,6,7,11b-hexahydro-2H-pyrido[2,1-a]isoquinolin-2-yl]-carbamic acid tert-butyl ester. Light yellow solid, MS (ISP) 360.3 (M+H)+.

Example 11

1-((RS,RS,RS)-2-Amino-9,10-dimethoxy-1,3,4,6,7,11b-hexahydro-2H-pyrido[2,1-a]isoquinolin-3-yl)-4-ethyl-pyrrolidin-2-one

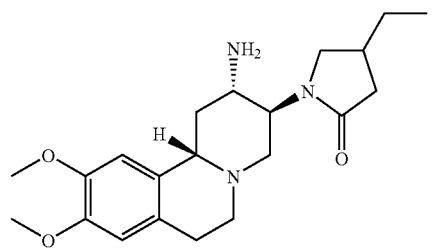

a) (RS,RS,RS)-[3-(3-Chloromethyl-pentanoylamino)-9,10-dimethoxy-1,3,4,6,7,11b-hexahydro-2H-pyrido[2,1-a]isoquinolin-2-yl]-carbamic acid tert-butyl ester The title compound was produced in accordance with the general method of Example 5c from (RS,RS,RS)-(3-amino-9,10-dimethoxy-1,3,4,6,7,11b-hexahydro-2H-pyrido[2,1-a]isoquinolin-2-yl)-carbamic acid tert-butyl ester (Example 5b) and 3-(chloromethyl)-valeryl chloride (*J. Korean Chem. Soc.* 1991, 35, 756). White solid, MS (ISP) 510.4 (M+H)$^+$.

b) (RS,RS,RS)-[3-(4-Ethyl-2-oxo-pyrrolidin-1-yl)-9,10-dimethoxy-1,3,4,6,7,11b-hexahydro-2H-pyrido [2,1-a]isoquinolin-2-yl]-carbamic acid tert-butyl ester The title compound was produced in accordance with the general method of Example 5d from (RS,RS,RS)-[3-(3-chloromethyl-pentanoylamino)-9,10-dimethoxy-1,3,4,6,7,11b-hexahydro-2H-pyrido [2,1-a]isoquinolin-2-yl]-carbamic acid tert-butyl ester. Light yellow solid, MS (ISP) 474.2 (M+H)$^+$.

c) 1-((RS,RS,RS)-2-Amino-9,10-dimethoxy-1,3,4,6,7,11b-hexahydro-2H-pyrido [2,1-a]isoquinolin-3-yl)-4-ethyl-pyrrolidin-2-one The title compound was produced in accordance with the general method of Example 1e from (RS,RS,RS)-[3-(4-ethyl-2-oxo-pyrrolidin-1-yl)-9,10-dimethoxy-1,3,4,6,7,11b-hexahydro-2H-pyrido[2,1-a]isoquinolin-2-yl]-carbamic acid tert-butyl ester. Light yellow solid, MS (ISP) 374.5 (M+H)$^+$.

Example 12

(RS,RS,RS)-1-(2-Amino-9,10-dimethoxy-1,3,4,6,7,11b-hexahydro-2H-pyrido [2,1-a]isoquinolin-3-yl)-5,6-dihydro-1H-pyridin-2-one

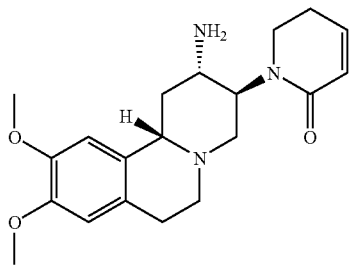

a) (RS,RS,RS)-(3-But-3-enylamino-9,10-dimethoxy-1,3,4,6,7,11b-hexahydro-2H-pyrido[2,1-a]isoquinolin-2-yl)-carbamic acid tert-butyl ester 4-Bromo-2-butene (60 mg, 0.45 mmol) and triethylamine (49 mg, 0.49 mmol) were added to a solution of (RS,RS,RS)-(3-amino-9,10-dimethoxy-1,3,4,6,7,11b-hexahydro-2H-pyrido [2,1-a]isoquinolin-2-yl)-carbamic acid tert-butyl ester (Example 5b; 153 mg, 0.41 mmol), and the mixture was heated at reflux, then after 18 h another portion of 4-bromo-2-butene (60 mg, 0.45 mmol) and triethylamine (49 mg, 0.49 mmol) was added. After another 24 h at reflux, the reaction mixture was poured onto ice and partitioned between 1 M aq. sodium hydroxide solution and ethyl acetate. The organic layer was washed with brine, dried (MgSO$_4$), and evaporated. Chromatography (SiO$_2$, CH$_2$Cl$_2$/MeOH/NH$_4$OH 95:5:0.25) afforded the title compound (77 mg, 44%). Off-white solid, MS (ISP) 432.4 (M+H)$^+$.

b) (RS,RS,RS)-[3-(Acryloyl-but-3-enyl-amino)-9,10-dimethoxy-1,3,4,6,7,11b-hexahydro-2H-pyrido[2,1-a]isoquinolin-2-yl]-carbamic acid tert-butyl ester Acryloyl chloride (18 mg, 0.20 mmol) was added dropwise at 0° C. to a solution of (RS,RS,RS)-(3-but-3-enylamino-9,10-dimethoxy-1,3,4,6,7,11b-hexahydro-2H-pyrido[2,1-a]isoquinolin-2-yl)-carbamic acid tert-butyl ester (77 mg, 0.18 mmol) and triethylamine (20 mg, 0.20 mmol) in dichloromethane (1.5 mL). After 30 min at 0° C. the reaction mixture was partitioned between 2 M aq. sodium carbonate solution and ethyl acetate. The organic layer was washed with brine, dried (MgSO$_4$), and evaporated. Chromatography (SiO$_2$, CH$_2$Cl$_2$/MeOH/NH$_4$OH 95:5:0.25) afforded the title compound (65 mg, 75%). White solid, MS (ISP) 486.5 (M+H)$^+$.

c) (RS,RS,RS)-[9,10-Dimethoxy-3-(6-oxo-3,6-dihydro-2H-pyridin-1-yl)-1,3,4,6,7,11b-hexahydro-2H-pyrido [2,1-a]isoquinolin-2-yl]-carbamic acid tert-butyl ester Tetraisopropyl orthotitanate (7.6 mg, 27 μmol) and Bis(tricyclohexylphosphine)-benzylideneruthenium(IV)dichloride (11 mg, 13 μmol) were added to a solution of (RS,RS,RS)-[3-(acryloyl-but-3-enyl-amino)-9,10-dimethoxy-1,3,4,6,7,11b-hexahydro-2H-pyrido[2,1-a]isoquinolin-2-yl]-carbamic acid tert-butyl ester (65 mg, 0.13 mmol) in dichloromethane (2.5 mL). The reaction mixture was stirred 45 min at r.t., then partitioned between ethyl acetate and water. The organic layer was washed with brine, dried (MgSO$_4$), and evaporated. Chromatography (SiO$_2$, CH$_2$Cl$_2$/MeOH/NH$_4$OH 95:5:0.25) afforded the title compound (59 mg, 96%). White solid, MS (ISP) 458.4 (M+H)$^+$.

d) (RS,RS,RS)-1-(2-Amino-9,10-dimethoxy-1,3,4,6,7,11b-hexahydro-2H-pyrido[2,1-a]isoquinolin-3-yl)-5,6-dihydro-1H-pyridin-2-one The title compound was produced in accordance with the general method of Example 1e from (RS,RS,RS)-[9,10-dimethoxy-3-(6-oxo-3,6-dihydro-2H-pyridin-1-yl)-1,3,4,6,7,11b-hexahydro-2H-pyrido[2,1-a]isoquinolin-2-yl]-carbamic acid tert-butyl ester. White foam, MS (ISP) 358.2 (M+H)$^+$.

Example 13

1-((RS,RS,RS)-2-Amino-9,10-dimethoxy-1,3,4,6,7,11b-hexahydro-2H-pyrido[2,1-a]isoquinolin-3-yl)-azepan-2-one

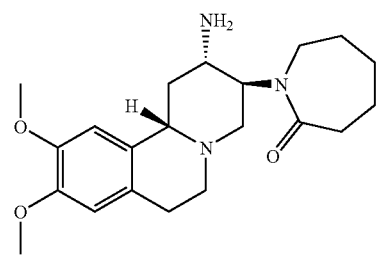

a) (RS,RS,RS)-2-Benzylamino-9,10-dimethoxy-1,3,4,6,7,11b-hexahydro-2H-pyrido[2,1-a]isoquinoline-3-carboxylic acid ethyl ester Trifluoroacetic acid (20 mL) was added at 0° C. to a solution of 2-amino-9,10-dimethoxy-1,6,7,11b-tetrahydro-4H-pyrido[2,1-a]isoquinoline-3-carboxylic acid ethyl ester (Example 1a; 2.00 g, 6.02 mmol) in tetrahydrofuran (20 mL), then after 30 min the homogeneous solution was treated with sodium borohydride (474 mg, 12.0 mmol) and stirred for another 40 min. The reaction mixture was concentrated in vacuo and the residue partitioned between 2 M aq. sodium hydroxide solution and dichloromethane. The organic layer was washed with brine, dried (MgSO$_4$) and evaporated. The residue was dissolved in methanol (37 mL) and acetic acid (9 mL) and treated with benzaldehyde (723 mg, 6.81 mmol), then sodium cyanoborohydride (526 mg, 7.95 mmol) was added portionwise at r.t. over 1 h. The reaction mixture was stirred another 15 min, then partitioned between sat. aq. sodium hydrogencarbonate solution and dichloromethane. The organic layer was washed with brine, dried (MgSO$_4$), and evaporated. Chromatrography of the residue (SiO$_2$, CH$_2$Cl$_2$/EtOAc 4:1, after elution of dibenzylated side-product, CH$_2$Cl$_2$/MeOH/NH$_4$OH 95:5:0.25) afforded the title compound (1.31 g, 51%). Red oil, MS (ISP) 425.2 (M+H)$^+$.

b) (RS,RS,RS)-2-(Benzyl-tert-butoxycarbonyl-amino)-9,10-dimethoxy-1,3,4,6,7,11b-hexahydro-2H-pyrido [2,1-a] isoquinoline-3-carboxylic acid ethyl ester Di-tert-butyl-dicarbonate (752 mg, 3.38 mmol) was added at r.t. to solution of (RS,RS,RS)-2-benzylamino-9,10-dimethoxy-1,3,4,6,7,11b-hexahydro-2H-pyrido[2,1-a]isoquinoline-3-carboxylic acid ethyl ester (1.30 g, 3.07 mmol) in dichloromethane (13 mL). After 16 h the solution was evaporated and the residue chromatographed (SiO$_2$, heptane-EtOAc gradient) to produce the title compound (1.24 g, 77%). Yellow foam, MS (ISP) 525.3 (M+H)$^+$.

c) (RS,RS,RS)-[2-(Benzyl-tert-butoxycarbonyl-amino)-9,10-dimethoxy-1,3,4,6,7,11b-hexahydro-2H-pyrido [2,1-a] isoquinolin-3-yl]-carbamic acid benzyl ester Potassium hydroxide pellets (86%, 1.53 g, 23.4 mmol) were added to a solution of (RS,RS,RS)-2-(benzyl-tert-butoxycarbonyl-amino)-9,10-dimethoxy-1,3,4,6,7,11b-hexahydro-2H-pyrido[2,1-a]isoquinoline-3-carboxylic acid ethyl ester (1.20 g, 2.28 mmol) in water/tetrahydrofuran 1:1 (24 mL), and the mixture was heated at reflux for 72 h. After cooling, the solution was neutralized with 1 M aq. potassium phosphate buffer (pH 6.85) and extracted three times with dichloromethane. The organic layers were pooled, dried (MgSO$_4$), and evaporated. The residue was suspended in toluene (24 mL) and treated with triethylamine (230 mg, 2.28 mmol) and diphenylphosphoryl azide (659 mg, 2.28 mmol). The reaction was kept at r.t. for 90 min and heated at 80° C. for 90 min, then benzyl alcohol (369 mg, 3.41 mmol) was added, and the reaction temperature was kept at 100° C. for 18 h. The reaction mixture was diluted with dichloromethane and washed with 10% aq. citric acid solution, 1 M aq. sodium hydroxide solution, and brine, dried (MgSO$_4$), and evaporated. Chromatography (SiO$_2$, heptane/EtOAc gradient) afforded the title compound (805 mg, 59%). Light yellow foam, MS (ISP) 602.3 (M+H)$^+$.

d) (RS,RS,RS)-(3-Amino-9,10-dimethoxy-1,3,4,6,7,11b-hexahydro-2H-pyrido[2,1-a]isoquinolin-2-yl)-benzyl-carbamic acid tert-butyl ester A solution of (RS,RS,RS)-[2-(benzyl-tert-butoxycarbonyl-amino)-9,10-dimethoxy-1,3,4,6,7,11b-hexahydro-2H-pyrido[2,1-a]isoquinolin-3-yl]-carbamic acid benzyl ester (802 mg, 1.33 mmol) in acetic acid (24 mL) was hydrogenated (1 bar, r.t., 3 h) in the presence of palladium (10% on activated charcoal, 40 mg), then the catalyst was removed by filtration and the filtrate evaporated. Chromatography (SiO$_2$, CH$_2$Cl$_2$/MeOH/NH$_4$OH 90:10:0.25) afforded the title compound (402 mg, 65%). Light yellow foam, MS (ISP) 468.4 (M+H)$^+$.

e) (RS,RS,RS)-Benzyl-[3-(6-chloro-hexanoylamino)-9,10-dimethoxy-1,3,4,6,7,11b-hexahydro-2H-pyrido[2,1-a]isoquinolin-2-yl]-carbamic acid tert-butyl ester The title compound was produced in accordance with the general method of Example 5c from (RS,RS,RS)-(3-amino-9,10-dimethoxy-1,3,4,6,7,11b-hexahydro-2H-pyrido[2,1-a]isoquinolin-2-yl)-benzyl-carbamic acid tert-butyl ester and 6-chlorohexanoyl chloride. Yellow oil, MS (ISP) 600.4 (M+H)$^+$.

f) (RS,RS,RS)-Benzyl-[9,10-dimethoxy-3-(2-oxo-azepan-1-yl)-1,3,4,6,7,11b-hexahydro-2H-pyrido[2,1-a]isoquinolin-2-yl]-carbamic acid tert-butyl ester The title compound was produced in accordance with the general method of Example 5d from (RS,RS,RS)-benzyl-[3-(6-chloro-hexanoylamino)-9,10-dimethoxy-1,3,4,6,7,11b-hexahydro-2H-pyrido [2,1-a]isoquinolin-2-yl]-carbamic acid tert-butyl ester. Off-white solid, MS (ISP) 564.4 (M+H)$^+$.

g) (RS,RS,RS)-1-(2-Benzylamino-9,10-dimethoxy-1,3,4,6,7,11b-hexahydro-2H-pyrido[2,1-a]isoquinolin-3-yl)-azepan-2-one The title compound was produced in accordance with the general method of Example 1e from (RS,RS,RS)-benzyl-[9,10-dimethoxy-3-(2-oxo-azepan-1-yl)-1,3,4,6,7,11b-hexahydro-2H-pyrido [2,1-a]isoquinolin-2-yl]-carbamic acid tert-butyl ester. Light yellow solid, MS (ISP) 464.5 (M+H)$^+$.

h) 1-((RS,RS,RS)-2-Amino-9,10-dimethoxy-1,3,4,6,7,11b-hexahydro-2H-pyrido [2,1-a]isoquinolin-3-yl)-azepan-2-one A solution of (RS,RS,RS)-1-(2-benzylamino-9,10-dimethoxy-1,3,4,6,7,11b-hexahydro-2H-pyrido[2,1-a]isoquinolin-3-yl)-azepan-2-one (35 mg, 75 µmol) was hydrogenated (3 bar, r.t., 3 h) in the presence of palladium (10% on activated charcoal), then the catalyst was removed by filtration and the filtrate evaporated. Chromatography (SiO$_2$, CH$_2$Cl$_2$/MeOH/NH$_4$OH 95:5:0.25) afforded the title compound (10 mg, 43%). Light yellow solid, MS (ISP) 374.2 (M+H)$^+$.

Example 14

(RS,RS,RS)-3-(1,1-Dioxo-1,2-thiazolidin-2-yl)-9,10-dimethoxy-1,3,4,6,7,11b-hexahydro-2H-pyrido[2,1-a]isoquinolin-2-ylamine

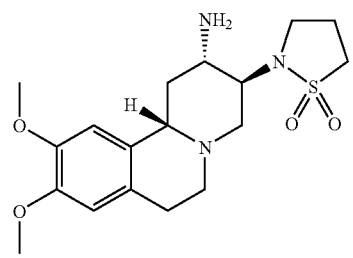

a) (RS,RS,RS)-[3-(3-Chloro-propane-1-sulfonylamino)-9,10-dimethoxy-1,3,4,6,7,11b-hexahydro-2H-pyrido[2,1-a]isoquinolin-2-yl]-carbamic acid tert-butyl ester The title compound was produced in accordance with the general method of Example 5c from (RS,RS,RS)-(3-amino-9,10-dimethoxy-1,3,4,6,7,11b-hexahydro-2H-pyrido[2,1-a]

isoquinolin-2-yl)-carbamic acid tert-butyl ester (Example 5b) and 3-chloropropanesulfonyl chloride. White solid, MS (ISP) 516.3 (M–H)⁻.

b) (RS,RS,RS)-[3-(1,1-Dioxoisothiazolidin-2-yl)-9,10-dimethoxy-1,3,4,6,7,11b-hexahydro-2H-pyrido [2,1-a]isoquinolin-2-yl]-carbamic acid tert-butyl ester The title compound was produced in accordance with the general method of Example 5d from (RS,RS,RS)-[3-(3-chloro-propane-1-sulfonylamino)-9,10-dimethoxy-1,3,4,6,7,11b-hexahydro-2H-pyrido[2,1-a]isoquinolin-2-yl]-carbamic acid tert-butyl ester. Off-white solid, MS (ISP) 482.3 (M+H)⁺.

c) (RS,RS,RS)-3-(1,1-Dioxo-1,2-thiazolidin-2-yl)-9,10-dimethoxy-1,3,4,6,7,11b-hexahydro-2H-pyrido [2,1-a]isoquinolin-2-ylamine The title compound was produced in accordance with the general method of Example 1e from (RS,RS,RS)-[3-(1,1-dioxoisothiazolidin-2-yl)-9,10-dimethoxy-1,3,4,6,7,11b-hexahydro-2H-pyrido [2,1-a]isoquinolin-2-yl]-carbamic acid tert-butyl ester. White foam, MS (ISP) 382.3 (M+H)⁺.

Example 15

(RS,RS,RS)-3-(1,1-Dioxo[1,2]thiazinan-2-yl)-9,10-dimethoxy-1,3,4,6,7,11b-hexahydro-2H-pyrido [2,1-a]isoquinolin-2-ylamine

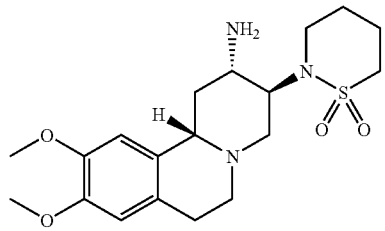

a) (RS,RS,RS)-[3-(4-Chloro-butane-1-sulfonylamino)-9,10-dimethoxy-1,3,4,6,7,11b-hexahydro-2H-pyrido[2,1-a]isoquinolin-2-yl]-carbamic acid tert-butyl ester The title compound was produced in accordance with the general method of Example 5c from (RS,RS,RS)-(3-amino-9,10-dimethoxy-1,3,4,6,7,11b-hexahydro-2H-pyrido[2,1-a]isoquinolin-2-yl)-carbamic acid tert-butyl ester (Example 5b) and 4-chlorobutanesulfonyl chloride (DE1300933). White solid, MS (ISP) 532.3 (M+H)⁺.

b) (RS,RS,RS)-[3-(1,1-Dioxo[1,2]thiazinan-2-yl)-9,10-dimethoxy-1,3,4,6,7,11b-hexahydro-2H-pyrido [2,1-a]isoquinolin-2-yl]-carbamic acid tert-butyl ester The title compound was produced in accordance with the general method of Example 5d from (RS,RS,RS)-[3-(4-chloro-butane-1-sulfonylamino)-9,10-dimethoxy-1,3,4,6,7,11b-hexahydro-2H-pyrido [2,1-a]isoquinolin-2-yl]-carbamic acid tert-butyl ester. White solid, MS (ISP) 496.3 (M+H)⁺.

c) (RS,RS,RS)-3-(1,1-Dioxo [1,2]thiazinan-2-yl)-9,10-dimethoxy-1,3,4,6,7,11b-hexahydro-2H-pyrido [2,1-a]isoquinolin-2-ylamine The title compound was produced in accordance with the general method of Example 1e from (RS,RS,RS)-[3-(1,1-dioxo[1,2]thiazinan-2-yl)-9,10-dimethoxy-1,3,4,6,7,11b-hexahydro-2H-pyrido[2,1-a]isoquinolin-2-yl]-carbamic acid tert-butyl ester. White solid, MS (ISP) 396.3 (M+H)⁺.

Example 16

(S,S,S)-3-(1,1-Dioxo-[1,2]thiazinan-2-yl)-9,10-dimethoxy-1,3,4,6,7,11b-hexahydro-2H-pyrido[2,1-a]isoquinolin-2-ylamine

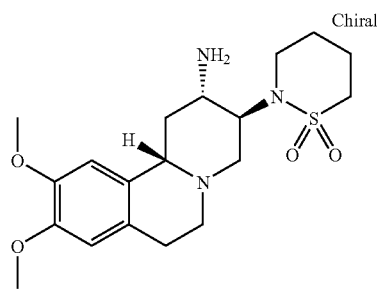

a) (S)-(6,7-Dimethoxy-1,2,3,4-tetrahydro-isoquinolin-1-yl)-acetic acid ethyl ester The title compound was produced in >99.5% e.e. from (6,7-Dimethoxy-1,2,3,4-tetrahydro-isoquinolin-1-yl)-acetic acid ethyl ester (*Synthesis* 1987, 474) by fractional crystallization with (−)-2'-nitrotartranilic acid, in accordance with the general procedure of Montzka et al. (U.S. Pat. No. 3,452,086). Light yellow solid, MS (ISP) 280.2 (M+H)⁺, $t_R$=6.4 min (Chiralcel® ODH 15×0.21 cm, heptane/2-propanol/triethylamine 75:25:0.15, flow rate 150 μL/min).

b) (S,S,S)-(3-Amino-9,10-dimethoxy-1,3,4,6,7,11b-hexahydro-2H-pyrido[2,1-a]isoquinolin-2-yl)-carbamic acid tert-butyl ester The title compound was produced from (S)-(6,7-dimethoxy-1,2,3,4-tetrahydro-isoquinolin-1-yl)-acetic acid ethyl ester, in accordance with the synthesis of the racemate, (RS,RS,RS)-(3-amino-9,10-dimethoxy-1,3,4,6,7,11b-hexahydro-2H-pyrido[2,1-a]isoquinolin-2-yl)-carbamic tert-butyl ester (Example 5b). Off-white solid, $t_R$=19.3 min (Chiralpak® AD 25×0.03 cm, heptane/ethanol/triethylamine 70:30:0.3, flow rate 4 μL/min).

c) (S,S,S)-3-(1,1-Dioxo-[1,2]thiazinan-2-yl)-9,10-dimethoxy-1,3,4,6,7,11b-hexahydro-2H-pyrido[2,1-a]isoquinolin-2-ylamine The title compound was produced in accordance with the synthesis of the racemate, (RS,RS,RS)-3-(1,1-dioxo[1,2]thiazinan-2-yl)-9,10-dimethoxy-1,3,4,6,7,11b-hexahydro-2H-pyrido[2,1-a]isoquinolin-2-ylamine (Example 15). Off-white foam.

Examples 17 and 18

(SR)-1-((RS,RS,RS)-2-Amino-9,10-dimethoxy-1,3,4,6,7,11b-hexahydro-2H-pyrido[2,1-a]isoquinolin-3-yl)-4-methyl-pyrrolidin-2-one

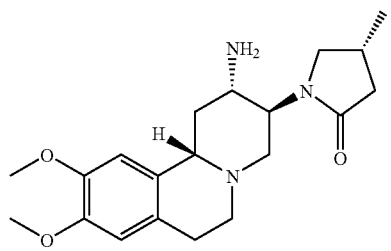

and (RS,RS,RS,RS)-1-(2-amino-9,10-dimethoxy-1,3,4,6,7,11b-hexahydro-2H-pyrido[2,1-a]isoquinolin-3-yl)-4-methyl-pyrrolidin-2-one

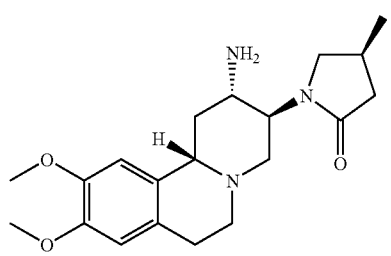

The title compounds were produced from 1-((RS,RS,RS)-2-amino-9,10-dimethoxy-1,3,4,6,7,11b-hexahydro-2H-pyrido[2,1-a]isoquinolin-3-yl)-4-methyl-pyrrolidin-2-one (Example 10) by chromatographic separation (SiO$_2$, CH$_2$Cl$_2$/MeOH/NH$_4$OH 90:10:0.25). (SR)-1-((RS,RS,RS)-2-Amino-9,10-dimethoxy-1,3,4,6,7,11b-hexahydro-2H-pyrido[2,1-a]isoquinolin-3-yl)-4-methyl-pyrrolidin-2-one: Light yellow foam, R$_f$=0.20.

(RS,RS,RS,RS)-1-(2-amino-9,10-dimethoxy-1,3,4,6,7,11b-hexahydro-2H-pyrido [2,1-a]isoquinolin-3-yl)-4-methyl-pyrrolidin-2-one: Light yellow solid, R$_f$=0.15.

Examples 19 and 20

(R)-1-((S,S,S)-2-Amino-9,10-dimethoxy-1,3,4,6,7,11b-hexahydro-2H-pyrido[2,1-a]isoquinolin-3-yl)-4-methyl-pyrrolidin-2-one

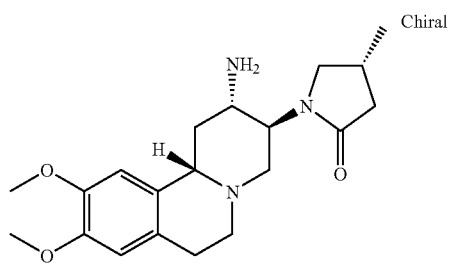

and (S)-1-((R,R,R)-2-amino-9,10-dimethoxy-1,3,4,6,7,11b-hexahydro-2H-pyrido[2,1-a]isoquinolin-3-yl)-4-methyl-pyrrolidin-2-one

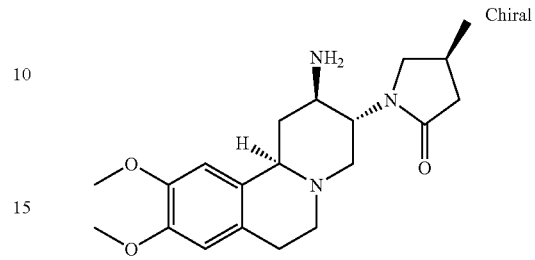

The title compounds were produced in accordance with the general method of Examples 6 and 7 from (SR)-1-((RS,RS,RS)-2-amino-9,10-dimethoxy-1,3,4,6,7,11b-hexahydro-2H-pyrido[2,1-a]isoquinolin-3-yl)-4-methyl-pyrrolidin-2-one (Example 17). (R)-1-((S,S,S)-2-Amino-9,10-dimethoxy-1,3,4,6,7,11b-hexahydro-2H-pyrido[2,1-a]isoquinolin-3-yl)-4-methyl-pyrrolidin-2-one: Off-white foam, t$_R$=40.1 min (Chiralpak® AD 25×0.46 cm, heptane/ethanol 80:20, flow rate 1 mL/min). (S)-1-((R,R,R)-2-amino-9,10-dimethoxy-1,3,4,6,7,11b-hexahydro-2H-pyrido[2,1-a]isoquinolin-3-yl)-4-methyl-pyrrolidin-2-one: Off-white foam, t$_R$=66.0 min (Chiralpak® AD 25×0.46 cm, heptane/ethanol 80:20, flow rate 1 mL/min).

Examples 21 and 22

(S,S,S,S)-1-(2-Amino-9,10-dimethoxy-1,3,4,6,7,11b-hexahydro-2H-pyrido[2,1-a]isoquinolin-3-yl)-4-methyl-pyrrolidin-2-one

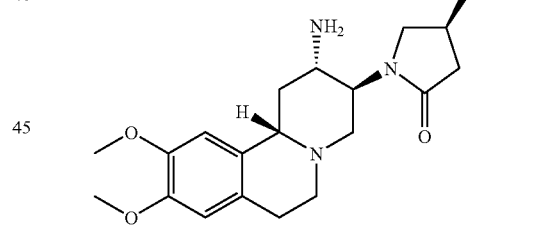

and (R,R,R,R)-1-(2-amino-9,10-dimethoxy-1,3,4,6,7,11b-hexahydro-2H-pyrido [2,1-a]isoquinolin-3-yl)-4-methyl-pyrrolidin-2-one

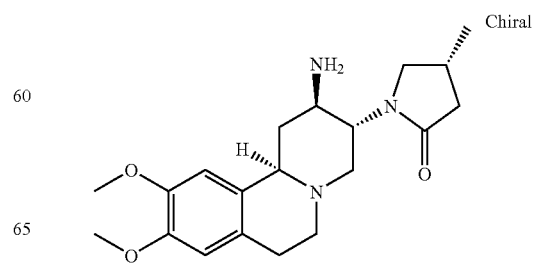

The title compounds were produced in accordance with the general method of Examples 6 and 7 from (RS,RS,RS,RS)-1-(2-amino-9,10-dimethoxy-1,3,4,6,7,11b-hexahydro-2H-pyrido [2,1-a]isoquinolin-3-yl)-4-methyl-pyrrolidin-2-one (Example 18). (S,S,S,S)-1-(2-Amino-9,10-dimethoxy-1,3,4,6,7,11b-hexahydro-2H-pyrido [2,1-a]isoquinolin-3-yl)-4-methyl-pyrrolidin-2-one: Off-white foam, $t_R$=29.4 min (Chiralpak® AD 25×0.46 cm, heptane/ethanol 80:20, flow rate 1 mL/min). (R,R,R,R)-1-(2-Amino-9,10-dimethoxy-1,3,4,6,7,11b-hexahydro-2H-pyrido[2,1-a]isoquinolin-3-yl)-4-methyl-pyrrolidin-2-one: Off-white foam, $t_R$=41.8 min (Chiralpak® AD 25×0.46 cm, heptane/ethanol 80:20, flow rate 1 mL/min).

Example 23

1-((RS,RS,RS)-2-Amino-9,10-dimethoxy-1,3,4,6,7,11b-hexahydro-2H-pyrido [2,1-a]isoquinolin-3-yl)-4-fluoromethyl-pyrrolidin-2-one

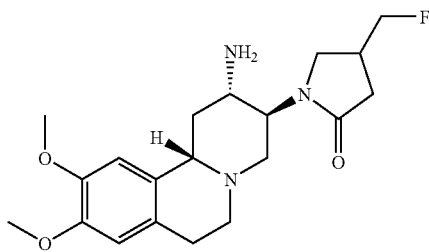

a) 4-Fluoromethyl-dihydro-furan-2-one

A solution of 4-hydroxymethyl-dihydro-furan-2-one (*Tetrahedron* 1994, 50, 6839; 1.02 g, 8.78 mmol) and bis(2-methoxyethyl)aminosulfur trifluoride (3.88 g, 17.6 mmol) in chloroform (4.4 mL) was stirred at 40° C. for 1 h, then poured onto ice and partitioned between sat. aq. sodium hydrogencarbonate solution and dichloromethane. The organic layer was washed with brine, dried (MgSO$_4$), and evaporated. Chromatography (SiO$_2$, heptane-ethyl acetate gradient) afforded the title compound (576 mg, 56%). Colourless liquid, MS (EI) 118.9 (M+H)$^+$.

b) 3-Chloromethyl-4-fluoro-butyryl chloride

A mixture of 4-fluoromethyl-dihydro-furan-2-one (871 mg, 7.37 mmol), thionyl chloride (4.39 g, 36.9 mmol), and zinc chloride (60 mg, 0.44 mmol) was stirred 72 h at 80° C., then excess thionyl chloride was removed by distillation. Kugelrohr distillation of the residue (85° C., 0.2 mbar) afforded the title compound (450 mg, 35%). Colourless liquid, $^1$H-NMR (300 MHz, CDCl$_3$): 4.65–4.55 (m, 1H), 4.50–4.40 (m, 1H), 3.70–3.60 (m, 2H), 3.25–3.05 (m, 2H), 2.80–2.60 (m, 1H).

c) (RS,RS,RS)-[3-(3-Chloromethyl-4-fluoro-butyrylamino)-9,10-dimethoxy-1,3,4,6,7,11b-hexahydro-2H-pyrido [2,1-a]isoquinolin-2-yl]-carbamic acid tert-butyl ester The title compound was produced in accordance with the general method of Example 5c from (RS,RS,RS)-(3-amino-9,10-dimethoxy-1,3,4,6,7,11b-hexahydro-2H-pyrido[2,1-a]isoquinolin-2-yl)-carbamic acid tert-butyl ester (Example 5b) and 3-chloromethyl-4-fluoro-butyryl chloride. White solid, MS (ISP) 514.5 (M+H)$^+$.

d) (RS,RS,RS)-[3-(4-Fluoromethyl-2-oxo-pyrrolidin-1-yl)-9,10-dimethoxy-1,3,4,6,7,11b-hexahydro-2H-pyrido[2,1-a]isoquinolin-2-yl]-carbamic acid tert-butyl ester The title compound was produced in accordance with the general method of Example 5d from (RS,RS,RS)-[3-(3-chloromethyl-4-fluoro-butyrylamino)-9,10-dimethoxy-1,3,4,6,7,11b-hexahydro-2H-pyrido[2,1-a]isoquinolin-2-yl]-carbamic acid tert-butyl ester. Off-white foam, MS (ISP) 478.5 (M+H)$^+$.

e) 1-((RS,RS,RS)-2-Amino-9,10-dimethoxy-1,3,4,6,7,11b-hexahydro-2H-pyrido[2,1-a]isoquinolin-3-yl)-4-fluoromethyl-pyrrolidin-2-one The title compound was produced in accordance with the general method of Example 1e from (RS,RS,RS)-[3-(4-fluoromethyl-2-oxo-pyrrolidin-1-yl)-9,10-dimethoxy-1,3,4,6,7,11b-hexahydro-2H-pyrido[2,1-a]isoquinolin-2-yl]-carbamic acid tert-butyl ester. Light yellow oil, MS (ISP) 378.5 (M+H)$^+$.

Example 24

1-((RS,RS,RS)-2-Amino-9,10-dimethoxy-1,3,4,6,7,11b-hexahydro-2H-pyrido [2,1-a]isoquinolin-3-yl)-5-methyl-piperidin-2-one

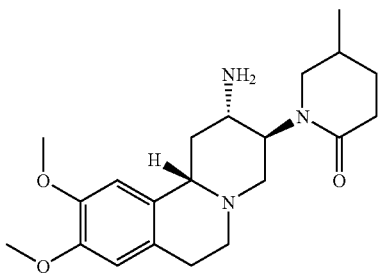

a) 5-Chloro-4-methyl-pentanoyl chloride

The title compound was produced in accordance with the general method of Example 23b from 5-methyl-tetrahydro-pyran-2-one (*Tetrahedron* 1995, 51, 6237). Colourless liquid, $^1$H-NMR (300 MHz, CDCl$_3$): 3.50–3.40 (m, 2H), 2.95 (td, 2H), 2.00–1.85 (m, 2H), 1.70–1.60 (m, 1H), 1.04 (d, 3H).

b) (RS,RS,RS)-[3-(5-Chloro-4-methyl-pentanoylamino)-9,10-dimethoxy-1,3,4,6,7,11b-hexahydro-2H-pyrido [2,1-a]isoquinolin-2-yl]-carbamic acid tert-butyl ester The title compound was produced in accordance with the general method of Example 5c from (RS,RS,RS)-(3-amino-9,10-dimethoxy-1,3,4,6,7,11b-hexahydro-2H-pyrido[2,1-a]isoquinolin-2-yl)-carbamic acid tert-butyl ester (Example 5b) and 5-chloro-4-methyl-pentanoyl chloride. Off-white solid, MS (ISP) 510.6 (M+H)$^+$.

c) (RS,RS,RS)-[9,10-Dimethoxy-3-(5-methyl-2-oxo-piperidin-1-yl)-1,3,4,6,7,11b-hexahydro-2H-pyrido[2,1-a]isoquinolin-2-yl]-carbamic acid tert-butyl ester The title compound was produced in accordance with the general method of Example 5d from (RS,RS,RS)-[3-(5-chloro-4-methyl-pentanoylamino)-9,10-dimethoxy-1,3,4,6,7,11b-hexahydro-2H-pyrido [2,1-a]isoquinolin-2-yl]-carbamic acid tert-butyl ester. Light yellow oil, MS (ISP) 474.5 (M+H)$^+$.

d) 1-((RS,RS,RS)-2-Amino-9,10-dimethoxy-1,3,4,6,7,11b-hexahydro-2H-pyrido [2,1-a]isoquinolin-3-yl)-5-methyl-piperidin-2-one The title compound was produced in accordance with the general method of Example 1e from (RS,RS,RS)-[9,10-dimethoxy-3-(5-methyl-2-oxo-piperidin-1-yl)-1,3,4,6,7,11b-hexahydro-2H-pyrido [2,1-a]isoquinolin-2-yl]-carbamic acid tert-butyl ester. Light yellow solid, MS (ISP) 374.5 (M+H)+.

Example 25

(RS,RS,RS)-N-(2-Amino-9,10-dimethoxy-1,3,4,6,7,11b-hexahydro-2H-pyrido [2,1-a]isoquinolin-3-yl)-propionamide

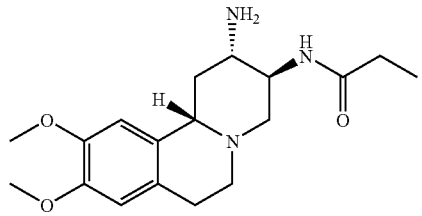

a) (RS,RS,RS)-(9,10-Dimethoxy-3-propionylamino-1,3,4,6,7,11b-hexahydro-2H-pyrido [2,1-a]isoquinolin-2-yl)-carbamic acid tert-butyl ester The title compound was produced in accordance with the general method of Example 5c from (RS,RS,RS)-(3-amino-9,10-dimethoxy-1,3,4,6,7,11b-hexahydro-2H-pyrido [2,1-a]isoquinolin-2-yl)-carbamic acid tert-butyl ester (Example 5b) and propionyl chloride. Light yellow solid, MS (ISP) 434.6 (M+H)+.

b) (RS,RS,RS)-N-(2-Amino-9,10-dimethoxy-1,3,4,6,7,11b-hexahydro-2H-pyrido[2,1-a]isoquinolin-3-yl)-propionamide The title compound was produced in accordance with the general method of Example 1e from (RS,RS,RS)-(9,10-dimethoxy-3-propionylamino-1,3,4,6,7,11b-hexahydro-2H-pyrido [2,1-a]isoquinolin-2-yl)-carbamic acid tert-butyl ester. Off-white solid, MS (ISP) 334.5 (M+H)+.

Example 26

(RS,RS,RS)-N-(2-Amino-9,10-dimethoxy-1,3,4,6,7,11b-hexahydro-2H-pyrido [2,1-a]isoquinolin-3-yl)-butyramide

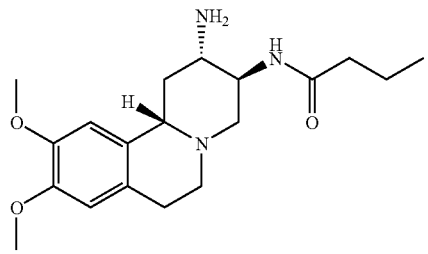

The title compound was produced in accordance with the general methods of Example 5c and 1e from (RS,RS,RS)-(3-amino-9,10-dimethoxy-1,3,4,6,7,11b-hexahydro-2H-pyrido[2,1-a]isoquinolin-2-yl)-carbamic acid tert-butyl ester (Example 5b) and butyryl chloride. Yellow solid, MS (ISP) 348.5 (M+H)+.

Example 27

Cyclopropanecarboxylic acid ((RS,RS,RS)-2-amino-9,10-dimethoxy-1,3,4,6,7,11b-hexahydro-2H-pyrido [2,1-a]isoquinolin-3-yl)-amide

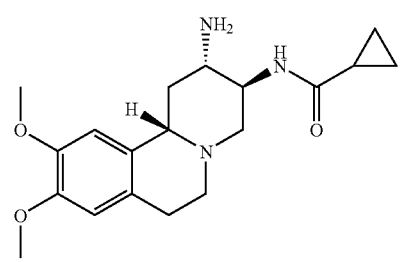

The title compound was produced in accordance with the general methods of Example 5c and 1e from (RS,RS,RS)-(3-amino-9,10-dimethoxy-1,3,4,6,7,11b-hexahydro-2H-pyrido[2,1-a]isoquinolin-2-yl)-carbamic acid tert-butyl ester (Example 5b) and cyclopropanecarbonyl chloride. Off-white solid, MS (ISP) 346.3 (M+H)+.

Examples 28 and 29

(SR)-1-((RS,RS,RS)-2-Amino-9,10-dimethoxy-1,3,4,6,7,11b-hexahydro-2H-pyrido [2,1-a]isoquinolin-3-yl)-4-fluoromethyl-pyrrolidin-2-one

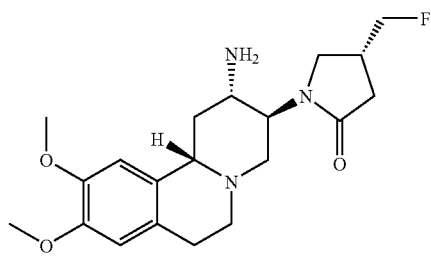

and (RS,RS,RS,RS)-1-(2-Amino-9,10-dimethoxy-1,3,4,6,7,11b-hexahydro-2H-pyrido[2,1-a]isoquinolin-3-yl)-4-fluoromethyl-pyrrolidin-2-one

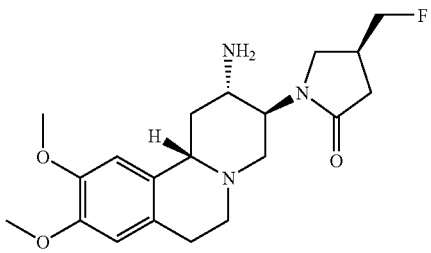

The title compounds were produced from 1-((RS,RS,RS)-2-amino-9,10-dimethoxy-1,3,4,6,7,11b-hexahydro-2H-pyrido[2,1-a]isoquinolin-3-yl)-4-fluoromethyl-pyrrolidin-2-one (Example 23) by chromatographic separation (SiO$_2$, CH$_2$Cl$_2$/MeOH/NH$_4$OH 80:1:0.2, then 95:5:0.25).

(SR)-1-((RS,RS,RS)-2-Amino-9,10-dimethoxy-1,3,4,6,7,11b-hexahydro-2H-pyrido[2,1-a]isoquinolin-3-yl)-4-fluoromethyl-pyrrolidin-2-one: Yellow oil, R$_f$=0.45 (CH$_2$Cl$_2$/MeOH/NH$_4$OH 90:10:0.25).

(RS,RS,RS,RS)-1-(2-Amino-9,10-dimethoxy-1,3,4,6,7,11b-hexahydro-2H-pyrido [2,1-a]isoquinolin-3-yl)-4-fluoromethyl-pyrrolidin-2-one: Light yellow solid, R$_f$=0.40 (CH$_2$Cl$_2$/MeOH/NH$_4$OH 90:10:0.25).

Example 30

(S)-1-((S,S,S)-2-Amino-9,10-dimethoxy-1,3,4,6,7,11b-hexahydro-2H-pyrido [2,1-a]isoquinolin-3-yl)-4-fluoromethyl-pyrrolidin-2-one Dihydrochloride

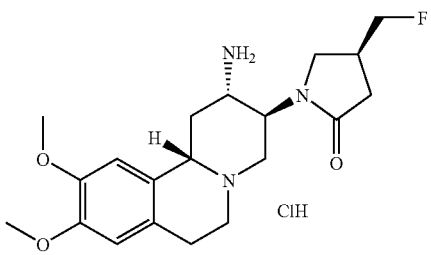

a) [(S,S,S)-3-(3-Chloromethyl-4-fluoro-butyrylamino)-9,10-dimethoxy-1,3,4,6,7,11b-hexahydro-2H-pyrido [2,1-a]isoquinolin-2-yl]-carbamic acid tert-butyl ester The title compound was produced in accordance with the general method of Example 5c from (S,S,S)-(3-amino-9,10-dimethoxy-1,3,4,6,7,11b-hexahydro-2H-pyrido[2,1-a]isoquinolin-2-yl)-carbamic acid tert-butyl ester (Example 16b) and 3-chloromethyl-4-fluoro-butyryl chloride (Example 23b). Off-white solid.

b) [(S,S,S)-3-((S)-4-Fluoromethyl-2-oxo-pyrrolidin-1-yl)-9,10-dimethoxy-1,3,4,6,7,11b-hexahydro-2H-pyrido[2,1-a]isoquinolin-2-yl]-carbamic acid tert-butyl ester and [(S,S,S)-3-((R)-4-fluoromethyl-2-oxo-pyrrolidin-1-yl)-9,10-dimethoxy-1,3,4,6,7,11b-hexahydro-2H-pyrido[2,1-a]isoquinolin-2-yl]-carbamic acid tert-butyl ester Sodium hydride (55–65% dispersion in oil, 1.14 g, 28.5 mmol) was added to a suspension of [(S,S,S)-3-(3-chloromethyl-4-fluoro-butyrylamino)-9,10-dimethoxy-1,3,4,6,7,11b-hexahydro-2H-pyrido[2,1-a]isoquinolin-2-yl]-carbamic acid tert-butyl ester (6.72 g, 13.1 mmol) in N,N-dimethylformamide (95 mL) at r.t., then after 1 h the reaction mixture was poured onto ice and partitioned between ethyl acetate and water. The organic layer was washed with brine, dried (MgSO$_4$), and evaporated. Chromatography (SiO$_2$, cyclohexane/2-propanol 4:1) afforded [(S,S,S)-3-((S)-4-fluoromethyl-2-oxo-pyrrolidin-1-yl)-9,10-dimethoxy-1,3,4,6,7,11b-hexahydro-2H-pyrido[2,1-a]isoquinolin-2-yl]-carbamic acid tert-butyl ester (2.40 g, 38%) and the epimer, [(S,S,S)-3-((R)-4-fluoromethyl-2-oxo-pyrrolidin-1-yl)-9,10-dimethoxy-1,3,4,6,7,11b-hexahydro-2H-pyrido [2,1-a]isoquinolin-2-yl]-carbamic acid tert-butyl ester (2.73 g, 44%).

[(S,S,S)-3-((S)-4-Fluoromethyl-2-oxo-pyrrolidin-1-yl)-9,10-dimethoxy-1,3,4,6,7,11b-hexahydro-2H-pyrido [2,1-a]isoquinolin-2-yl]-carbamic acid tert-butyl ester: Light yellow foam, R$_f$=0.6 (SiO$_2$, cyclohexane/2-propanol 1:1).

[(S,S,S)-3-((R)-4-Fluoromethyl-2-oxo-pyrrolidin-1-yl)-9,10-dimethoxy-1,3,4,6,7,11b-hexahydro-2H-pyrido[2,1-a]isoquinolin-2-yl]-carbamic acid tert-butyl ester: Light yellow foam, R$_f$=0.4 (SiO$_2$, cyclohexane/2-propanol 1:1).

c) (S)-1-((S,S,S)-2-Amino-9,10-dimethoxy-1,3,4,6,7,11b-hexahydro-2H-pyrido[2,1-a]isoquinolin-3-yl)-4-fluoromethyl-pyrrolidin-2-one dihydrochloride

[(S,S,S)-3-((S)-4-Fluoromethyl-2-oxo-pyrrolidin-1-yl)-9,10-dimethoxy-1,3,4,6,7,11b-hexahydro-2H-pyrido [2,1-a]isoquinolin-2-yl]-carbamic acid tert-butyl ester (2.40 g, 5.02 mmol) was converted to (S)-1-((S,S,S)-2-amino-9,10-dimethoxy-1,3,4,6,7,11b-hexahydro-2H-pyrido [2,1-a]isoquinolin-3-yl)-4-fluoromethyl-pyrrolidin-2-one in accordance with the general method of Example 1e. The product was dissolved in 2-propanol (10 mL) and treated with hydrogen chloride (5–6 M in 2-propanol, 37 mL). The suspension formed was stirred for 64 h at r.t., then the precipitate was collected by filtration and dried, to afford the title compound (2.04 g, 91%). White solid, m.p. >300° C.

Example 31

(R)-1-((S,S,S)-2-Amino-9,10-dimethoxy-1,3,4,6,7,11b-hexahydro-2H-pyrido [2,1-a]isoquinolin-3-yl)-4-fluoromethyl-pyrrolidin-2-one dihydrochloride

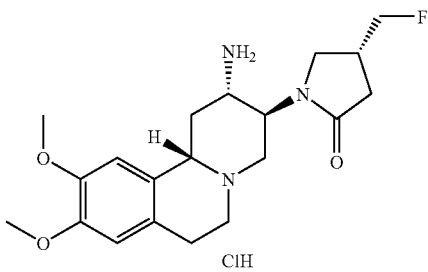

The title compound was produced in accordance with the general method of Example 30c from [(S,S,S)-3-((R)-4-fluoromethyl-2-oxo-pyrrolidin-1-yl)-9,10-dimethoxy-1,3,4,6,7,11b-hexahydro-2H-pyrido [2,1-a]isoquinolin-2-yl]-carbamic acid tert-butyl ester (Example 30b). White solid, m.p. >300° C.

Example 32

3-((RS,RS,RS)-2-Amino-9,10-dimethoxy-1,3,4,6,7,11b-hexahydro-2H-pyrido [2,1-a]isoquinolin-3-yl)-oxazolidin-2-one

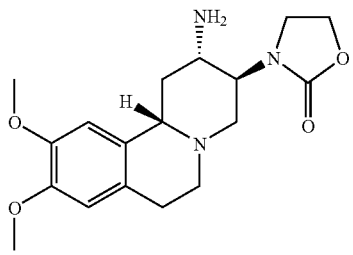

The title compound was produced in accordance with the general methods of Example 5c, 5d, and 1e from (RS,RS,RS)-(3-amino-9,10-dimethoxy-1,3,4,6,7,11b-hexahydro-2H-pyrido[2,1-a]isoquinolin-2-yl)-carbamic acid tert-butyl ester (Example 5b) and 2-chloroethyl chloroformate. Light yellow solid, MS (ISP) 348.5 (M+H)+.

Example 33

3-((RS,RS,RS)-2-Amino-9,10-dimethoxy-1,3,4,6,7,11b-hexahydro-2H-pyrido [2,1-a]isoquinolin-3-yl)-[1,3]oxazinan-2-one

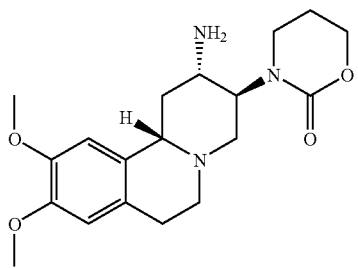

a) ((RS,RS,RS)-2-tert-Butoxycarbonylamino-9,10-dimethoxy-1,3,4,6,7,11b-hexahydro-2H-pyrido[2,1-a]isoquinolin-3-yl)-carbamic acid 3-chloro-propyl ester The title compound was produced in accordance with the general method of Example 5c from (RS,RS,RS)-(3-amino-9,10-dimethoxy-1,3,4,6,7,11b-hexahydro-2H-pyrido[2,1-a]isoquinolin-2-yl)-carbamic acid tert-butyl ester (Example 5b) and 3-chloropropyl chloroformate. Off-white solid, MS (ISP) 498.4 (M+H)+.

b) [(RS,RS,RS)-9,10-Dimethoxy-3-(2-oxo-[1,3]oxazinan-3-yl)-1,3,4,6,7,11b-hexahydro-2H-pyrido[2,1-a]isoquinolin-2-yl]-carbamic acid tert-butyl ester The title compound was produced in accordance with the general method of Example 5d from ((RS,RS,RS)-2-tert-butoxycarbonylamino-9,10-dimethoxy-1,3,4,6,7,11b-hexahydro-2H-pyrido[2,1-a]isoquinolin-3-yl)-carbamic acid 3-chloro-propyl ester. Off-white solid, MS (ISP) 462.4 (M+H)+.

c) 3-((RS,RS,RS)-2-Amino-9,10-dimethoxy-1,3,4,6,7,11b-hexahydro-2H-pyrido[2,1-a]isoquinolin-3-yl)-[1,3]oxazinan-2-one The title compound was produced in accordance with the general method of Example 1e from [(RS,RS,RS)-9,10-dimethoxy-3-(2-oxo-[1,3]oxazinan-3-yl)-1,3,4,6,7,11b-hexahydro-2H-pyrido[2,1-a]isoquinolin-2-yl]-carbamic acid tert-butyl ester. Yellow solid, MS (ISP) 362.5 (M+H)+.

Example 34

1-((RS,RS,RS)-2-Amino-9,10-dimethoxy-1,3,4,6,7,11b-hexahydro-2H-pyrido [2,1-a]isoquinolin-3-yl)-5-methyl-pyrrolidin-2-one

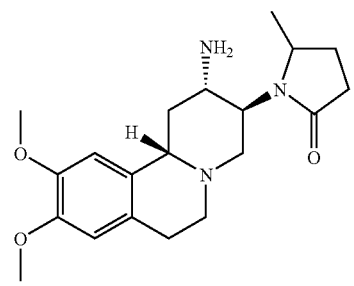

a) 4-Chloro-pentanoyl chloride

The title compound was produced in accordance with the general method of Example 23b from γ-valerolactone. Colourless liquid, 1H-NMR (300 MHz, CDCl₃): 4.10–4.00 (m, 1H), 3.25–3.05 (m, 2H), 2.25–2.15 (m, 1H), 2.05–1.95 (m, 1H), 1.55 (d, 3H).

b) [(RS,RS,RS)-3-(4-Chloro-pentanoylamino)-9,10-dimethoxy-1,3,4,6,7,11b-hexahydro-2H-pyrido[2,1-a]isoquinolin-2-yl]-carbamic acid tert-butyl ester The title compound was produced in accordance with the general method of Example 5c from (RS,RS,RS)-(3-amino-9,10-dimethoxy-1,3,4,6,7,11b-hexahydro-2H-pyrido[2,1-a]isoquinolin-2-yl)-carbamic acid tert-butyl ester (Example 5b) and 4-chloro-pentanoyl chloride. Off-white solid, MS (ISP) 496.4 (M+H)+.

c) 1-((RS,RS,RS)-2-Amino-9,10-dimethoxy-1,3,4,6,7,11b-hexahydro-2H-pyrido [2,1-a]isoquinolin-3-yl)-5-methyl-pyrrolidin-2-one The title compound was produced in accordance with the general methods of Example 5d and 1e from [(RS,RS,RS)-3-(4-chloro-pentanoylamino)-9,10-dimethoxy-1,3,4,6,7,11b-hexahydro-2H-pyrido[2,1-a]isoquinolin-2-yl]-carbamic acid tert-butyl ester. Yellow solid, MS (ISP) 360.1 (M+H)+.

Example 35

3-((RS,RS,RS)-2-Amino-9,10-dimethoxy-1,3,4,6,7,11b-hexahydro-2H-pyrido [2,1-a]isoquinolin-3-yl)-5-fluoromethyl-oxazolidin-2-one

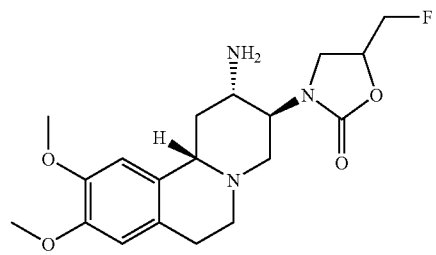

a) [(RS,RS,RS)-3-(2-Chloro-1-fluoromethyl-ethoxycarbonylamino)-9,10-dimethoxy-1,3,4,6,7,11b-hexahydro-2H-pyrido[2,1-a]isoquinolin-2-yl]-carbamic acid tert-butyl ester Pyridine (69 mg, 0.87 mmol) was added dropwise at 0° C. to a solution of 1-chloro-3-fluoroisopropanol (34 mg, 0.29 mmol) in dichloromethane (0.8 mL), then the solution was allowed to reach r.t. over 2 h. After cooling again to 0° C., (RS,RS,RS)-(3-amino-9,10-dimethoxy-1,3,4,6,7,11b-hexahydro-2H-pyrido[2,1-a]isoquinolin-2-yl)-carbamic acid tert-butyl ester (Example 5b, 100 mg, 0.26 mmol), pyridine (23 mg, 0.29 mmol), and 4-dimethylaminopyridine (1 mg, 8 μmol) were added. The reaction mixture was allowed to reach r.t. over 16 h, then partitioned between sat. aq. ammonium chloride solution and ether. The organic layer was washed with water, dried (MgSO$_4$), and evaporated. Chromatography (SiO$_2$, heptane-ethyl acetate gradient) produced the title compound (65 mg, 48%). White solid, MS (ISP) 516.5 (M+H)$^+$.

b) [(RS,RS,RS)-3-(5-Fluoromethyl-2-oxo-oxazolidin-3-yl)-9,10-dimethoxy-1,3,4,6,7,11b-hexahydro-2H-pyrido [2,1-a]isoquinolin-2-yl]-carbamic acid tert-butyl ester The title compound was produced in accordance with the general method of Example 5d from [(RS,RS,RS)-3-(2-chloro-1-fluoromethyl-ethoxycarbonylamino)-9,10-dimethoxy-1,3,4,6,7,11b-hexahydro-2H-pyrido [2,1-a]isoquinolin-2-yl]-carbamic acid tert-butyl ester. White solid, MS (ISP) 480.5 (M+H)$^+$.

c) 3-((RS,RS,RS)-2-Amino-9,10-dimethoxy-1,3,4,6,7,11b-hexahydro-2H-pyrido [2,1-a]isoquinolin-3-yl)-5-fluoromethyl-oxazolidin-2-one The title compound was produced in accordance with the general method of Example 1e from [(RS,RS,RS)-3-(5-fluoromethyl-2-oxo-oxazolidin-3-yl)-9,10-dimethoxy-1,3,4,6,7,11b-hexahydro-2H-pyrido [2,1-a]isoquinolin-2-yl]-carbamic acid tert-butyl ester. Yellow solid, MS (ISP) 380.4 (M+H)$^+$.

Example 36

1-((RS,RS,RS)-2-Amino-9,10-dimethoxy-1,3,4,6,7,11b-hexahydro-2H-pyrido[2,1-a]isoquinolin-3-yl)-3-methyl-pyrrolidin-2-one

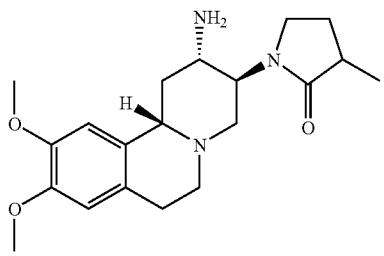

a) 4-Chloro-2-methyl-butyryl chloride

The title compound was produced in accordance with the general method of Example 23b from γ-valerolactone. Colourless liquid, $^1$H-NMR (300 MHz, CDCl$_3$): 3.61 (t, 2H), 3.25–3.15 (m, 1H), 2.40–2.25 (m, 1H), 2.00–1.85 (m, 1H), 1.36 (d, 3H).

b) [(RS,RS,RS)-3-(4-Chloro-2-methyl-butyrylamino)-9,10-dimethoxy-1,3,4,6,7,11b-hexahydro-2H-pyrido[2,1-a]isoquinolin-2-yl]-carbamic acid tert-butyl ester The title compound was produced in accordance with the general method of Example 5c from (RS,RS,RS)-(3-amino-9,10-dimethoxy-1,3,4,6,7,11b-hexahydro-2H-pyrido [2,1-a]isoquinolin-2-yl)-carbamic acid tert-butyl ester (Example 5b) and 4-chloro-2-methyl-butyryl chloride. Off-white solid, MS (ISP) 496.4 (M+H)$^+$.

c) 1-((RS,RS,RS)-2-Amino-9,10-dimethoxy-1,3,4,6,7,11b-hexahydro-2H-pyrido [2,1-a]isoquinolin-3-yl)-3-methyl-pyrrolidin-2-one The title compound was produced in accordance with the general method of Example 5d and 1e from [(RS,RS,RS)-3-(4-chloro-2-methyl-butyrylamino)-9,10-dimethoxy-1,3,4,6,7,11b-hexahydro-2H-pyrido[2,1-a]isoquinolin-2-yl]-carbamic acid tert-butyl ester. Yellow solid, MS (ISP) 360.5 (M+H)$^+$.

Example 37

3-((RS,RS,RS)-2-Amino-9,10-dimethoxy-1,3,4,6,7,11b-hexahydro-2H-pyrido [2,1-a]isoquinolin-3-yl)-5-methyl-oxazolidin-2-one

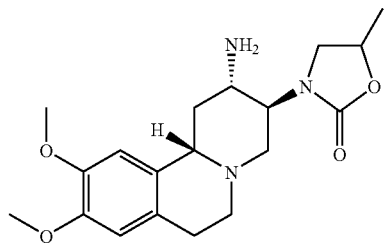

a) ((RS,RS,RS)-2-tert-Butoxycarbonylamino-9,10-dimethoxy-1,3,4,6,7,11b-hexahydro-2H-pyrido[2,1-a]isoquinolin-3-yl)-carbamic acid 2-chloro-1-methyl-ethyl ester The title compound was produced in accordance with the general method of Example 35a from (RS,RS,RS)-(3-amino-9,10-dimethoxy-1,3,4,6,7,11b-hexahydro-2H-pyrido [2,1-a]isoquinolin-2-yl)-carbamic acid tert-butyl ester (Example 5b) and 1-chloro-propan-2-ol (J. Chem. Soc. Perkin Trans. 1 1983, 3019). Off-white solid, MS (ISP) 498.4 (M+H)$^+$.

b) [(RS,RS,RS)-9,10-Dimethoxy-3-(5-methyl-2-oxo-oxazolidin-3-yl)-1,3,4,6,7,11b-hexahydro-2H-pyrido[2,1-a]isoquinolin-2-yl]-carbamic acid tert-butyl ester The title compound was produced in accordance with the general method of Example 5d from ((RS,RS,RS)-2-tert-butoxycarbonylamino-9,10-dimethoxy-1,3,4,6,7,11b-hexahydro-2H-pyrido[2,1-a]isoquinolin-3-yl)-carbamic acid 2-chloro-1-methyl-ethyl ester. White solid, MS (ISP) 462.4 (M+H)$^+$.

c) 3-((RS,RS,RS)-2-Amino-9,10-dimethoxy-1,3,4,6,7,11b-hexahydro-2H-pyrido [2,1-a]isoquinolin-3-yl)-5-methyl-oxazolidin-2-one The title compound was produced in accordance with the general method of Example 1e from [(RS,RS,RS)-9,10-dimethoxy-3-(5-methyl-2-oxo-oxazolidin-3-yl)-1,3,4,6,7,11b-hexahydro-2H-pyrido[2,1-a]isoquinolin-2-yl]-carbamic acid tert-butyl ester. Light yellow solid, MS (ISP) 362.4 (M+H)$^+$.

Galenical Examples

Example A

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
| --- | --- |
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| Ingredients | |
| --- | --- |
| Compound of formula (I) | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of polyethylene glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Ingredients | |
| --- | --- |
| Capsule contents | |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| Ingredients | |
| --- | --- |
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavouring additives and filled into sachets.

What is claimed is:

1. A compound of formula (I)

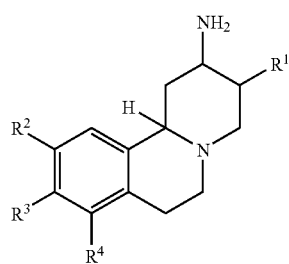

wherein
R$^1$ is —C(O)—N(R$^5$)R$^6$ or —N(R$^5$)R$^6$;
R$^2$, R$^3$ and R$^4$ are each independently hydrogen, halogen, hydroxy, lower alkyl, lower alkoxy, lower alkenyl, substituted lower alkyl, substituted lower alkoxy, or substituted lower alkenyl, wherein substituted lower alkyl, substituted lower alkoxy and substituted lower alkenyl are lower alkyl, lower alkoxy and lower alkenyl, respectively, which are independently substituted by a group selected from the group consisting of lower alkoxycarbonyl, aryl and heterocyclyl;

$R^5$ is hydrogen, lower alkyl, halogenated lower alkyl or cycloalkyl;

$R^6$ is lower alkylsulfonyl, halogenated lower alkylsulfonyl, cycloalkylsulfonyl, lower alkylcarbonyl, halogenated lower alkylcarbonyl, or cycloalkylcarbonyl; or $R^5$ and $R^6$ together with the nitrogen atom to which they are attached form a 4-, 5-, 6- or 7-membered saturated or unsaturated non-aromatic heterocyclic ring optionally containing a further heteroatom selected from nitrogen, oxygen and sulfur, said heterocyclic ring being optionally mono-, di-, or tri-substituted, independently, with a group selected from the group consisting of lower alkyl, halogenated lower alkyl, oxo, dioxo and cyano;

or a pharmaceutically acceptable salt thereof.

2. The compound according to claim 1, wherein $R^1$ is —C(O)—N($R^5$)$R^6$.

3. The compound according to claim 1, wherein $R^1$ is —N($R^5$)$R^6$.

4. The compound according to claim 1, wherein $R^2$, $R^3$ and $R^4$ are each independently hydrogen, hydroxy or lower alkoxy.

5. The compound according to claim 4, wherein $R^2$ is lower alkoxy.

6. The compound according to claim 4, wherein $R^3$ is lower alkoxy.

7. The compound according to claim 4, wherein $R^4$ is hydrogen.

8. The compound according to claim 1, wherein $R^5$ is hydrogen, lower alkyl or halogenated lower alkyl.

9. The compound according to claim 1, wherein $R^6$ is lower alkylsulfonyl, lower alkylcarbonyl or cycloalkylcarbonyl.

10. The compound according to claim 1, wherein $R^5$ and $R^6$ together with the nitrogen atom to which they are attached form a 4-, 5-, 6- or 7-membered saturated or unsaturated non-aromatic heterocyclic ring optionally containing a further heteroatom selected from a sulfur and oxygen, said heterocyclic ring being optionally mono- or di-substituted, independently, with a group selected from the group consisting of lower alkyl, halogenated lower alkyl, oxo, dioxo and cyano.

11. The compound according to claim 10, wherein $R^5$ and $R^6$ together with the nitrogen atom to which they are attached are selected from the group consisting of pyrrolidine, pyrrolidin-2-one, 4-methyl-pyrrolidin-2-one, 4-ethyl-pyrrolidin-2-one, 3-methyl-pyrrolidin-2-one, 5-methyl-pyrrolidin-2-one, 4-fluoro-methyl-pyrrolidin-2-one, pyrrolidine-2-carbonitrile, piperidine, piperidin-2-one, 4-methyl-piperidin-2-one, 5-methyl-piperidin-2-one, 5,6-dihydro-1H-pyridin-2-one, thiazolidin-3-yl, 1,1-dioxo-1,2-thiazolidin-2-yl, 1,1-dioxo [1,2]thiazinan-2-yl, azetidine, azepan-2-one, oxazolidin-2-one, 5-methyl-oxazolidin-2-one, 5-fluoromethyl-oxazolidin-2-one, and [1,3]oxazinan-2-one.

12. The compound according to claim 1, selected from the group consisting of:

(RS,RS,RS)-(2-amino-9,10-dimethoxy-1,3,4,6,7,11b-hexahydro-2H-pyrido[2,1-a]isoquinolin-3-yl)-pyrrolidin-1-yl-methanone;

(RS,RS,RS)-(2-amino-9,10-dimethoxy-1,3,4,6,7,11b-hexahydro-2H-pyrido [2,1-a]isoquinolin-3-yl)-thiazolidin-3-yl-methanone;

(RS,RS,RS)-(2-amino-9,10-dimethoxy-1,3,4,6,7,11b-hexahydro-2H-pyrido [2,1-a]isoquinolin-3-yl)-azetidin-1-yl-methanone;

(SS)-1-((RS,RS,RS)-2-amino-9,10-dimethoxy-1,3,4,6,7,11b-hexahydro-2H-pyrido [2,1-a]isoquinoline-3-carbonyl)-pyrrolidine-2-carbonitrile;

1-((RS,RS,RS)-2-amino-9,10-dimethoxy-1,3,4,6,7,11b-hexahydro-2H-pyrido [2,1-a]isoquinolin-3-yl)-piperidin-2-one;

(−)-(S,S,S)-1-(2-amino-9,10-dimethoxy-1,3,4,6,7,11b-hexahydro-2H-pyrido [2,1-a]isoquinolin-3-yl)-piperidin-2-one;

(+)-(R,R,R)-1-(2-amino-9,10-dimethoxy-1,3,4,6,7,11b-hexahydro-2H-pyrido[2,1-a]isoquinolin-3-yl)-piperidin-2-one;

1-((RS,RS,RS)-2-amino-9,10-dimethoxy-1,3,4,6,7,11b-hexahydro-2H-pyrido [2,1-a]isoquinolin-3-yl)-4-methyl-piperidin-2-one;

(RS,RS,RS)-1-(2-amino-9,10-dimethoxy-1,3,4,6,7,11b-hexahydro-2H-pyrido [2,1-a]isoquinolin-3-yl)-pyrrolidin-2-one; and 1-((RS,RS,RS)-2-amino-9,10-dimethoxy-1,3,4,6,7,11b-hexahydro-2H-pyrido[2,1-a]isoquinolin-3-yl)-4-methyl-pyrrolidin-2-one;

or a pharmaceutically acceptable salt thereof.

13. The compound according to claim 1, selected from the group consisting of:

1-((RS,RS,RS)-2-amino-9,10-dimethoxy-1,3,4,6,7,11b-hexahydro-2H-pyrido [2,1-a]isoquinolin-3-yl)-4-ethyl-pyrrolidin-2-one;

(RS,RS,RS)-1-(2-amino-9,10-dimethoxy-1,3,4,6,7,11b-hexahydro-2H-pyrido[2,1-a]isoquinolin-3-yl)-5,6-dihydro-1H-pyridin-2-one;

1-((RS,RS,RS)-2-amino-9,10-dimethoxy-1,3,4,6,7,11b-hexahydro-2H-pyrido[2,1-a]isoquinolin-3-yl)-azepan-2-one;

(RS,RS,RS)-3-(1,1-dioxo-1,2-thiazolidin-2-yl)-9,10-dimethoxy-1,3,4,6,7,11b-hexahydro-2H-pyrido [2,1-a]isoquinolin-2-ylamine;

(RS,RS,RS)-3-(1,1-dioxo[1,2]thiazinan-2-yl)-9,10-dimethoxy-1,3,4,6,7,11b-hexahydro-2H-pyrido[2,1-a]isoquinolin-2-ylamine;

(S,S,S)-3-(1,1-dioxo-[1,2]thiazinan-2-yl)-9,10-dimethoxy-1,3,4,6,7,11b-hexahydro-2H-pyrido [2,1-a]isoquinolin-2-ylamine;

(SR)-1-((RS,RS,RS)-2-amino-9,10-dimethoxy-1,3,4,6,7,11b-hexahydro-2H-pyrido[2,1-a]isoquinolin-3-yl)-4-methyl-pyrrolidin-2-one;

(RS,RS,RS,RS)-1-(2-amino-9,10-dimethoxy-1,3,4,6,7,11b-hexahydro-2H-pyrido[2,1-a]isoquinolin-3-yl)-4-methyl-pyrrolidin-2-one;

(R)-1-((S,S,S)-2-amino-9,10-dimethoxy-1,3,4,6,7,11b-hexahydro-2H-pyrido [2,1-a]isoquinolin-3-yl)-4-methyl-pyrrolidin-2-one and (S)-1-((R,R,R)-2-amino-9,10-dimethoxy-1,3,4,6,7,11b-hexahydro-2H-pyrido [2,1-a]isoquinolin-3-yl)-4-methyl-pyrrolidin-2-one;

or a pharmaceutically acceptable salt thereof.

14. The compound according to claim 1, selected from the group consisting of:

(S,S,S,S)-1-(2-amino-9,10-dimethoxy-1,3,4,6,7,11b-hexahydro-2H-pyrido [2,1-a]isoquinolin-3-yl)-4-methyl-pyrrolidin-2-one;

(R,R,R,R)-1-(2-amino-9,10-dimethoxy-1,3,4,6,7,11b-hexahydro-2H-pyrido [2,1-a]isoquinolin-3-yl)-4-methyl-pyrrolidin-2-one;

1-((RS,RS,RS)-2-amino-9,10-dimethoxy-1,3,4,6,7,11b-hexahydro-2H-pyrido [2,1-a]isoquinolin-3-yl)-4-fluoromethyl-pyrrolidin-2-one;

1-((RS,RS,RS)-2-amino-9,10-dimethoxy-1,3,4,6,7,11b-hexahydro-2H-pyrido[2,1-a]isoquinolin-3-yl)-5-methyl-piperidin-2-one;

(RS,RS,RS)-N-(2-amino-9,10-dimethoxy-1,3,4,6,7,11b-hexahydro-2H-pyrido[2,1-a]isoquinolin-3-yl)-propionamide;

(RS,RS,RS)-N-(2-amino-9,10-dimethoxy-1,3,4,6,7,11b-hexahydro-2H-pyrido [2,1-a]isoquinolin-3-yl)-butyramide;

cydopropanecarboxylic acid ((2RS,3RS,11bRS)-2-amino-9,10-dimethoxy-1,3,4,6,7,11b-hexahydro-2H-pyrido [2,1-a]isoquinolin-3-yl)-amide;

(SR)-1-((RS,RS,RS)-2-amino-9,10-dimethoxy-1,3,4,6,7,11b-hexahydro-2H-pyrido [2,1-a]isoquinolin-3-yl)-4-fluoromethyl-pyrrolidin-2-one;

(RS,RS,RS,RS)-1-(2-amino-9,10-dimethoxy-1,3,4,6,7,11b-hexahydro-2H-pyrido [2,1-a]isoquinolin-3-yl)-4-fluoromethyl-pyrrolidin-2-one and (S)-1-((2S,3S,11bS)-2-amino-9,10-dimethoxy-1,3,4,6,7,11b-hexahydro-2H-pyrido [2,1-a]isoquinolin-3-yl)-4-fluoromethyl-pyrrolidin-2-one;

or a pharmaceutically acceptable salt thereof.

15. The compound according to claim 1, selected from the group consisting of:
(R)-1-((2S,3S,11bS)-2-amino-9,10-dimethoxy-1,3,4,6,7,11b-hexahydro-2H-pyrido [2,1-a]isoquinolin-3-yl)-4-fluoromethyl-pyrrolidin-2-one;

3-((RS,RS,RS)-2-amino-9,10-dimethoxy-1,3,4,6,7,11b-hexahydro-2H-pyrido [2,1-a]isoquinolin-3-yl)-oxazolidin-2-one;

3-((2RS,3RS,11bRS)-2-amino-9,10-dimethoxy-1,3,4,6,7,11b-hexahydro-2H-pyrido [2,1-a]isoquinolin-3-yl)-[1,3]oxazinan-2-one;

1-((2RS,3RS,11bRS)-2-amino-9,10-dimethoxy-1,3,4,6,7,11b-hexahydro-2H-pyrido [2,1-a]isoquinolin-3-yl)-5-methyl-pyrrolidin-2-one;

3-((2RS,3RS,11bRS)-2-amino-9,10-dimethoxy-1,3,4,6,7,11b-hexahydro-2H-pyrido [2,1-a]isoquinolin-3-yl)-5-fluoromethyl-oxazolidin-2-one;

1-((2RS,3RS,11bRS)-2-amino-9,10-dimethoxy-1,3,4,6,7,11b-hexahydro-2H-pyrido [2,1-a]isoquinolin-3-yl)-3-methyl-pyrrolidin-2-one; and 3-((2RS,3RS,11bRS)-2-amino-9,10-dimethoxy-1,3,4,6,7,11b-hexahydro-2H-pyrido [2,1-a]isoquinolin-3-yl)-5-methyl-oxazolidin-2-one;

or a pharmaceutically acceptable salt thereof.

16. The compound according to claim 12, selected from the group consisting of:
(RS,RS,RS)-(2-amino-9,10-dimethoxy-1,3,4,6,7,11b-hexahydro-2H-pyrido[2,1-a]isoquinolin-3-yl)-thiazolidin-3-yl-methanone;

(−)-(S,S,S)-1-(2-amino-9,10-dimethoxy-1,3,4,6,7,11b-hexahydro-2H-pyrido[2,1-a]isoquinolin-3-yl)-piperidin-2-one; and 1-((RS,RS,RS)-2-amino-9,10-dimethoxy-1,3,4,6,7,11b-hexahydro-2H-pyrido[2,1-a]isoquinolin-3-yl)-4-methyl-pyrrolidin-2-one;

or a pharmaceutically acceptable salt thereof.

17. The compound according to claim 13, selected from the group consisting of:
(RS,RS,RS)-1-(2-amino-9,10-dimethoxy-1,3,4,6,7,11b-hexahydro-2H-pyrido[2,1-a]isoquinolin-3-yl)-5,6-dihydro-1H-pyridin-2-one;

(S,S,S)-3-(1,1-dioxo-[1,2]thiazinan-2-yl)-9,10-dimethoxy-1,3,4,6,7,11b-hexahydro-2H-pyrido[2,1-a]isoquinolin-2-ylamine; and (R)-1-((S,S,S)-2-amino-9,10-dimethoxy-1,3,4,6,7,11b-hexahydro-2H-pyrido[2,1-a]isoquinolin-3-yl)-4-methyl-pyrrolidin-2-one;

or a pharmaceutically acceptable salt thereof.

18. The compound according to claim 14, wherein said compound is (S,S,S,S)-1-(2-amino-9,10-dimethoxy-1,3,4,6,7,11b-hexahydro-2H-pyrido[2,1-a]isoquinolin-3-yl)-4-methyl-pyrrolidin-2-one;

or a pharmaceutically acceptable salt thereof.

19. The compound according to claim 15, selected from the group consisting of:
(R)-1-((2S,3S,11bS)-2-amino-9,10-dimethoxy-1,3,4,6,7,11b-hexahydro-2H-pyrido[2,1-a]isoquinolin-3-yl)-4-fluoromethyl-pyrrolidin-2-one; and 3-((2RS,3RS,11bRS)-2-amino-9,10-dimethoxy-1,3,4,6,7,11b-hexahydro-2H-pyrido [2,1-a]isoquinolin-3-yl)-5-methyl-oxazolidin-2-one;

or a pharmaceutically acceptable salt thereof.

20. A pharmaceutical composition comprising a compound according to claim 1 and a pharmaceutically acceptable carrier.

21. A method for the treatment of non-insulin dependent diabetes mellitus in a patient in need thereof, comprising administering to said patient a compound according to claim 1 in an amount of from about 1 to 1000 mg per day.

22. The method according to claim 21, wherein the amount is from about 1 to 100 mg per day.

23. The compound according to claim 14, wherein said compound is 1-((RS,RS,RS)-2-amino-9,10-dimethoxy-1,3,4,6,7,11b-hexahydro-2H-pyrido[2,1-a]isoquinolin-3-yl)-5-methyl-piperdin-2-one, or a pharmaceutically acceptable salt thereof.

24. The compound according to claim 14, wherein said compound is (S)-1-((2S,3S,11bS)-2-amino-9,10-dimethoxy-1,3,4,6,7,11b-hexahydro-2H-pyrido[2,1-a]isoquinolin-3-yl)-4-fluoromethyl-pyrrolidin-2-one, or a pharmaceutically acceptable salt thereof.

* * * * *